US012007385B2

(12) United States Patent
Peterson et al.

(10) Patent No.: US 12,007,385 B2
(45) Date of Patent: Jun. 11, 2024

(54) SYSTEMS AND METHODS FOR DETECTING A BRAIN CONDITION

(71) Applicant: REGENTS OF THE UNIVERSITY OF MINNESOTA, Minneapolis, MN (US)

(72) Inventors: Gregory Kermit Peterson, Centerville, MN (US); Justin Theodore Nelson, Vadnais Heights, MN (US); Gregory J. Sherwood, White Bear Lake, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/941,364

(22) Filed: Sep. 9, 2022

(65) Prior Publication Data

US 2023/0184741 A1 Jun. 15, 2023

Related U.S. Application Data

(63) Continuation of application No. 16/656,159, filed on Oct. 17, 2019, now Pat. No. 11,442,056.
(Continued)

(51) Int. Cl.
*G01N 33/497* (2006.01)
*G01N 1/22* (2006.01)
*G01N 27/22* (2006.01)

(52) U.S. Cl.
CPC ......... *G01N 33/497* (2013.01); *G01N 1/2226* (2013.01); *G01N 27/227* (2013.01); *G01N 2001/2244* (2013.01); *G01N 33/4972* (2013.01)

(58) Field of Classification Search
CPC ... A61B 2505/01; A61B 5/082; A61B 5/4064; G01N 1/22; G01N 1/2226;
(Continued)

(56) References Cited

U.S. PATENT DOCUMENTS 3,661,528 A 5/1972 Falk
5,704,368 A 1/1998 Asano et al.
(Continued)

FOREIGN PATENT DOCUMENTS

CN 1301342 6/2001
CN 107076693 9/2017
(Continued)

OTHER PUBLICATIONS

"First Office Action," for Chinese Patent Application No. 201980014220.0 dated Feb. 9, 2023 (14 pages) with English summary.
(Continued)

*Primary Examiner* — Maureen Wallenhorst
(74) *Attorney, Agent, or Firm* — Pauly, DeVries Smith & Deffner LLC

(57) ABSTRACT

Embodiments herein include a method for detecting a brain condition in a subject. The method can include obtaining a breath sample from the subject and contacting it with a chemical sensor element, where the chemical sensor element includes a plurality of discrete graphene varactors. The method can include sensing and storing capacitance of the discrete graphene varactors to obtain a sample data set and classifying the sample data set into one or more preestablished brain condition classifications. Other embodiments are also included herein.

16 Claims, 9 Drawing Sheets

Related U.S. Application Data

(60) Provisional application No. 62/747,939, filed on Oct. 19, 2018.

(58) Field of Classification Search
CPC ......... G01N 2001/2244; G01N 27/227; G01N 27/22; G01N 2800/2871; G01N 33/497; G01N 33/4972; G01N 33/4975; G01N 33/6896; H01L 29/1606
USPC ....... 436/63, 149, 151, 181, 900; 422/82.01, 422/82.02, 83, 84, 88, 90, 98
See application file for complete search history.

(56) References Cited

U.S. PATENT DOCUMENTS

| | | | |
|---|---|---|---|
| 5,834,626 A | 11/1998 | De Castro et al. | |
| 6,085,576 A | 7/2000 | Sunshine et al. | |
| 6,149,624 A | 11/2000 | McShane | |
| 6,192,168 B1 | 2/2001 | Feldstein et al. | |
| 6,248,078 B1 | 6/2001 | Risby et al. | |
| 6,312,390 B1 | 11/2001 | Phillips et al. | |
| 6,480,734 B1 | 11/2002 | Zhang et al. | |
| 6,599,253 B1 | 7/2003 | Baum et al. | |
| 6,712,770 B2 | 3/2004 | Lin et al. | |
| 6,726,637 B2 | 4/2004 | Phillips et al. | |
| 6,781,690 B2 | 8/2004 | Armstrong et al. | |
| 6,938,619 B1 | 9/2005 | Hickle | |
| 6,955,652 B1 | 10/2005 | Baum et al. | |
| 6,978,182 B2 | 12/2005 | Mazar et al. | |
| 7,032,431 B2 | 4/2006 | Baum et al. | |
| 7,123,359 B2 | 10/2006 | Armstrong et al. | |
| 7,177,686 B1 | 2/2007 | Turcott et al. | |
| 7,426,848 B1 | 9/2008 | Li et al. | |
| 7,459,312 B2 | 12/2008 | Chen et al. | |
| 7,704,214 B2 | 4/2010 | Meixner et al. | |
| 7,809,441 B2 | 10/2010 | Kane et al. | |
| 7,871,572 B2 | 1/2011 | Yang et al. | |
| 7,972,277 B2 | 7/2011 | Oki et al. | |
| 7,992,422 B2 | 8/2011 | Leddy et al. | |
| 8,043,860 B2 | 10/2011 | Leznoff et al. | |
| 8,052,933 B2 | 11/2011 | Schirmer et al. | |
| 8,080,206 B2 | 12/2011 | Leddy et al. | |
| 8,124,419 B2 | 2/2012 | Grigorian et al. | |
| 8,153,439 B2 | 4/2012 | Zamborini et al. | |
| 8,154,093 B2 | 4/2012 | Passmore et al. | |
| 8,157,730 B2 | 4/2012 | Tucker et al. | |
| 8,222,041 B2 | 7/2012 | Pearton et al. | |
| 8,244,355 B2 | 8/2012 | Bennett et al. | |
| 8,366,630 B2 | 2/2013 | Haick et al. | |
| 8,479,731 B2 | 7/2013 | Heinonen et al. | |
| 8,481,324 B2 | 7/2013 | Nakhoul et al. | |
| 8,494,606 B2 | 7/2013 | Debreczeny et al. | |
| 8,529,459 B2 | 9/2013 | Stahl et al. | |
| 8,597,953 B2 | 12/2013 | Haick et al. | |
| 8,747,325 B2 | 6/2014 | Bacal et al. | |
| 8,828,713 B2 | 9/2014 | Ren et al. | |
| 8,835,984 B2 | 9/2014 | Ren et al. | |
| 8,848,189 B2 | 9/2014 | Goldshtein et al. | |
| 8,955,367 B2 | 2/2015 | Gouma et al. | |
| 9,011,779 B1 | 4/2015 | Anglin, Jr. et al. | |
| 9,029,168 B2 | 5/2015 | Mannoor et al. | |
| 9,103,775 B2 | 8/2015 | Bradley et al. | |
| 9,147,851 B1 | 9/2015 | Bartsch et al. | |
| 9,299,238 B1 | 3/2016 | Ahmad et al. | |
| 9,315,848 B2 | 4/2016 | Haick et al. | |
| 9,316,637 B2 | 4/2016 | Ren et al. | |
| 9,324,825 B2 | 4/2016 | Ravesi et al. | |
| 9,357,946 B2 | 6/2016 | Johnson et al. | |
| 9,366,664 B2 | 6/2016 | Anglin, Jr. et al. | |
| 9,513,244 B2 | 12/2016 | Koester | |
| 9,528,979 B2 | 12/2016 | Haick et al. | |
| 9,618,476 B2 | 4/2017 | Goldsmith | |
| 9,643,186 B1 | 5/2017 | Ahmad et al. | |
| 9,696,311 B2 | 7/2017 | Haick et al. | |
| 9,765,395 B2 | 9/2017 | Goldsmith | |
| 9,936,897 B2 | 4/2018 | Carlson et al. | |
| 10,034,621 B2 | 7/2018 | Wondka et al. | |
| 10,046,323 B2 | 8/2018 | Bos | |
| 10,070,804 B2 | 9/2018 | Eichler | |
| 10,191,005 B2 | 1/2019 | Koester | |
| 10,852,264 B2 | 12/2020 | Kelly et al. | |
| 11,143,662 B2 | 10/2021 | Edmonds et al. | |
| 11,166,636 B2 | 11/2021 | Erdman et al. | |
| 11,191,457 B2 | 12/2021 | Sherwood et al. | |
| 11,262,354 B2 | 3/2022 | Sherwood | |
| 11,442,056 B2 | 9/2022 | Peterson et al. | |
| 2002/0123749 A1 | 9/2002 | Jain et al. | |
| 2002/0142477 A1 | 10/2002 | Lewis et al. | |
| 2003/0051733 A1 | 3/2003 | Kotmel et al. | |
| 2003/0060726 A1 | 3/2003 | Lin et al. | |
| 2003/0176804 A1 | 9/2003 | Melker | |
| 2004/0039295 A1 | 2/2004 | Olbrich et al. | |
| 2005/0103343 A1 | 5/2005 | Gosweiler | |
| 2006/0130557 A1 | 6/2006 | Leddy et al. | |
| 2006/0263255 A1 | 11/2006 | Han et al. | |
| 2006/0270940 A1 | 11/2006 | Tsukashima et al. | |
| 2007/0048181 A1 | 3/2007 | Chang et al. | |
| 2007/0083094 A1 | 4/2007 | Colburn et al. | |
| 2007/0167853 A1 | 7/2007 | Melker et al. | |
| 2007/0229818 A1 | 10/2007 | Duan et al. | |
| 2007/0265509 A1 | 11/2007 | Burch et al. | |
| 2008/0021339 A1 | 1/2008 | Gabriel et al. | |
| 2008/0038154 A1 | 2/2008 | Longbottom et al. | |
| 2008/0146890 A1 | 6/2008 | LeBoeuf et al. | |
| 2008/0161709 A1 | 7/2008 | Bradley | |
| 2008/0183910 A1 | 7/2008 | Natoli et al. | |
| 2008/0227073 A1 | 9/2008 | Bardsley et al. | |
| 2008/0228098 A1 | 9/2008 | Popov et al. | |
| 2008/0317636 A1 | 12/2008 | Brahim et al. | |
| 2009/0054799 A1 | 2/2009 | Vrtis et al. | |
| 2009/0112115 A1 | 4/2009 | Huang et al. | |
| 2010/0024533 A1 | 2/2010 | Kimura et al. | |
| 2010/0081955 A1 | 4/2010 | Wood et al. | |
| 2010/0085067 A1 | 4/2010 | Gabriel et al. | |
| 2010/0087749 A1 | 4/2010 | Tovey | |
| 2010/0137733 A1 | 6/2010 | Wang et al. | |
| 2010/0147303 A1 | 6/2010 | Jafari et al. | |
| 2010/0188069 A1 | 7/2010 | Ren et al. | |
| 2010/0198521 A1 | 8/2010 | Haick et al. | |
| 2010/0216175 A1 | 8/2010 | Melker et al. | |
| 2010/0273665 A1 | 10/2010 | Haick et al. | |
| 2011/0015872 A1 | 1/2011 | Haick et al. | |
| 2011/0017587 A1 | 1/2011 | Zhamu et al. | |
| 2011/0092839 A1 | 4/2011 | Alshaer et al. | |
| 2011/0143962 A1 | 6/2011 | Chaubron et al. | |
| 2011/0238319 A1 | 9/2011 | Adamko et al. | |
| 2011/0269632 A1 | 11/2011 | Haick et al. | |
| 2011/0283770 A1 | 11/2011 | Hok et al. | |
| 2012/0111093 A1 | 5/2012 | Brahim et al. | |
| 2012/0126111 A1 | 5/2012 | Chaubron et al. | |
| 2012/0156099 A1 | 6/2012 | Zhong et al. | |
| 2012/0166095 A1 | 6/2012 | Potyrailo et al. | |
| 2012/0203081 A1 | 8/2012 | LeBoeuf et al. | |
| 2012/0226111 A1 | 9/2012 | LeBoeuf et al. | |
| 2012/0226112 A1 | 9/2012 | LeBoeuf et al. | |
| 2012/0245434 A1 | 9/2012 | Haick et al. | |
| 2012/0245854 A1 | 9/2012 | Haick et al. | |
| 2012/0277794 A1 | 11/2012 | Kountotsis et al. | |
| 2012/0289838 A1 | 11/2012 | Varga et al. | |
| 2012/0326092 A1 | 12/2012 | Haick et al. | |
| 2013/0006068 A1 | 1/2013 | Gemer et al. | |
| 2013/0034190 A1 | 2/2013 | Tan et al. | |
| 2013/0034910 A1 | 2/2013 | Haick et al. | |
| 2013/0059758 A1 | 3/2013 | Haick et al. | |
| 2013/0060157 A1 | 3/2013 | Beard | |
| 2013/0102018 A1 | 4/2013 | Schentag et al. | |
| 2013/0143247 A1 | 6/2013 | Haick et al. | |
| 2013/0150261 A1 | 6/2013 | Haick et al. | |
| 2013/0165810 A1 | 6/2013 | Saatchi et al. | |
| 2013/0171733 A1 | 7/2013 | Haick et al. | |
| 2013/0178756 A1 | 7/2013 | Suzuki et al. | |
| 2013/0211207 A1 | 8/2013 | Joseph et al. | |
| 2013/0211852 A1 | 8/2013 | Roizen et al. | |
| 2013/0236981 A1 | 9/2013 | Haick et al. | |

(56) References Cited

U.S. PATENT DOCUMENTS

| | | |
|---|---|---|
| 2013/0253358 A1 | 9/2013 | Phillips et al. |
| 2013/0266668 A1 | 10/2013 | Safo et al. |
| 2013/0267862 A1 | 10/2013 | Jaffe et al. |
| 2013/0289368 A1 | 10/2013 | Covington et al. |
| 2013/0296823 A1 | 11/2013 | Melker et al. |
| 2013/0331723 A1 | 12/2013 | Hernandez-Silveira et al. |
| 2013/0334579 A1 | 12/2013 | Accardi et al. |
| 2014/0018691 A1 | 1/2014 | McNeill et al. |
| 2014/0039206 A1 | 2/2014 | Jonsson et al. |
| 2014/0041436 A1 | 2/2014 | Knott et al. |
| 2014/0051956 A1 | 2/2014 | Dalene et al. |
| 2014/0066800 A1 | 3/2014 | Takatori et al. |
| 2014/0094669 A1 | 4/2014 | Jaffe et al. |
| 2014/0145735 A1 | 5/2014 | Koester et al. |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0276168 A1 | 9/2014 | Satya et al. |
| 2014/0294675 A1 | 10/2014 | Melker et al. |
| 2014/0318535 A1 | 10/2014 | Bullock et al. |
| 2014/0330154 A1 | 11/2014 | Haveri |
| 2014/0364758 A1 | 12/2014 | Schindhelm et al. |
| 2014/0378790 A1 | 12/2014 | Cohen |
| 2015/0004169 A1 | 1/2015 | Kayed |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0065901 A1 | 3/2015 | Bhatnagar et al. |
| 2015/0105683 A1 | 4/2015 | Bos |
| 2015/0132858 A1 | 5/2015 | Ahmad et al. |
| 2015/0164373 A1 | 6/2015 | Davis et al. |
| 2015/0196251 A1 | 7/2015 | Outwater et al. |
| 2015/0217075 A1 | 8/2015 | Nair |
| 2015/0257676 A1 | 9/2015 | Fries |
| 2015/0265184 A1 | 9/2015 | Wondka et al. |
| 2015/0295562 A1 | 10/2015 | Agarwal et al. |
| 2015/0301021 A1 | 10/2015 | Haick et al. |
| 2015/0307936 A1 | 10/2015 | Goldsmith |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1 | 11/2015 | Anglin et al. |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0109440 A1 | 4/2016 | Sherwood |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0296168 A1 | 10/2016 | Abreu |
| 2016/0334381 A1 | 11/2016 | King-Smith et al. |
| 2016/0370337 A1 | 12/2016 | Blackley |
| 2017/0014043 A1 | 1/2017 | McDonnell |
| 2017/0035326 A1 | 2/2017 | King-Smith |
| 2017/0042435 A1 | 2/2017 | Vermeulen et al. |
| 2017/0050057 A1 | 2/2017 | Sabolis et al. |
| 2017/0053068 A1 | 2/2017 | Pillai et al. |
| 2017/0074857 A1 | 3/2017 | Dennis et al. |
| 2017/0105656 A1 | 4/2017 | Rigas |
| 2017/0227491 A1 | 8/2017 | Johnson et al. |
| 2017/0251952 A1 | 9/2017 | Harshman et al. |
| 2017/0254817 A1 | 9/2017 | Grafman et al. |
| 2017/0303822 A1 | 10/2017 | Allsworth et al. |
| 2017/0307562 A1 | 10/2017 | Goldsmith |
| 2017/0307576 A1 | 10/2017 | Anglin, Jr. et al. |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0037985 A1 | 2/2018 | Myers et al. |
| 2018/0078798 A1 | 3/2018 | Fabian et al. |
| 2018/0110444 A1 | 4/2018 | Sherwood et al. |
| 2018/0172590 A1 | 6/2018 | Marsh et al. |
| 2018/0202993 A1 | 7/2018 | Molina et al. |
| 2018/0228400 A1 | 8/2018 | Baba et al. |
| 2018/0328841 A1 | 11/2018 | Graham et al. |
| 2018/0336970 A1* | 11/2018 | Sherwood .............. A61B 5/082 |
| 2019/0025237 A1 | 1/2019 | Kelly et al. |
| 2019/0254538 A1 | 8/2019 | Erdman et al. |
| 2019/0331661 A1 | 10/2019 | Zhen et al. |
| 2019/0365283 A1 | 12/2019 | Chou et al. |
| 2020/0124588 A1 | 4/2020 | Peterson et al. |
| 2020/0166435 A1 | 5/2020 | Sherwood et al. |
| 2020/0178891 A1 | 6/2020 | Verbeck, IV et al. |
| 2020/0191737 A1 | 6/2020 | Sherwood et al. |
| 2020/0337566 A1 | 10/2020 | Peterson et al. |
| 2021/0148848 A1 | 5/2021 | Kelly et al. |
| 2022/0125325 A1 | 4/2022 | Erdman et al. |

FOREIGN PATENT DOCUMENTS

| | | |
|---|---|---|
| CN | 109270130 | 1/2019 |
| CN | 109310326 | 2/2019 |
| CN | 111801048 | 10/2020 |
| CN | 112930480 | 6/2021 |
| CN | 113747836 | 12/2021 |
| EP | 1764153 | 3/2007 |
| EP | 1806414 | 7/2007 |
| EP | 3093653 | 11/2016 |
| EP | 3210007 | 8/2017 |
| EP | 3431977 | 1/2019 |
| EP | 3439544 | 2/2019 |
| EP | 3867639 | 8/2021 |
| EP | 3962358 | 3/2022 |
| EP | 3755220 | 8/2022 |
| GB | 201402809 | 4/2014 |
| GB | 2523180 | 8/2015 |
| JP | H07507943 | 9/1995 |
| JP | 2005514081 | 5/2005 |
| JP | 2011102747 | 5/2011 |
| JP | 2011523363 | 8/2011 |
| JP | 2016022415 | 2/2016 |
| JP | 2017123912 | 7/2017 |
| JP | 2019020415 | 2/2019 |
| WO | 9920177 | 4/1999 |
| WO | 9947905 | 9/1999 |
| WO | 2001070114 | 9/2001 |
| WO | 2008088780 | 7/2008 |
| WO | 2009135070 | 11/2009 |
| WO | 2012059763 | 5/2012 |
| WO | 2013090999 | 6/2013 |
| WO | 2013095730 | 6/2013 |
| WO | 2013189502 | 12/2013 |
| WO | 2014193847 | 12/2014 |
| WO | 2015191558 | 12/2015 |
| WO | 2016064740 | 4/2016 |
| WO | 2016105464 | 6/2016 |
| WO | 2017218464 | 12/2017 |
| WO | 2018075731 | 4/2018 |
| WO | 2018213564 | 11/2018 |
| WO | 2019164925 | 8/2019 |
| WO | 2020081834 | 4/2020 |
| WO | 2020223208 | 11/2020 |

OTHER PUBLICATIONS

"Extended European Search Report," for European Patent Application No. 22189298.7 dated Dec. 12, 2022 (11 pages).

"Non-Final Office Action," for U.S. Appl. No. 16/860,529 dated Nov. 25, 2022 (51 pages).

"Response to Non-Final Rejection," mailed on Nov. 25, 2023 for U.S. Appl. No. 16/860,529, submitted via EFS-Web on Feb. 27, 2023, 11 pages.

(56) References Cited

OTHER PUBLICATIONS

Doran, Sophie L.F., et al. "Optimisation of sampling parameters for standardised exhaled breath sampling," Journal of Breath Research, vol. 12, No. 1, Dec. 6, 2017 (12 pages).
"10 Leading Causes of Death, United States," (NCIPC) NCfIPaC. Web-based Injury Statistics Query and Reporting System. https://webappa.cdc.gov/sasweb/ncipc/leadcause.html, as available on Feb. 23, 2018 (3 pages).
"Communication Pursuant to Article 94(3) EPC," for European Patent Application No. 15790739.5 dated Dec. 17, 2019 (5 pages).
"Communication Pursuant to Article 94(3) EPC," for European Patent Application No. 18180455.0 dated Dec. 20, 2019 (3 pages).
"Communication Pursuant to Article 94(3) EPC," for European Patent Application No. 18180455.0 dated Feb. 11, 2019 (6 pages).
"Communication Pursuant to Article 94(3) EPC," for European Patent Application No. 19711730.2 dated Aug. 27, 2021 (4 pages).
"European Search Report," for Dutch Patent Application No. 2019492 dated Apr. 12, 2018 (10 pages).
"European Search Report," for European Patent Application No. 18180455.0 dated Dec. 3, 2018 (5 pages).
"FDC1004 4-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments Aug. 2014—Revised Oct. 2016 (46 pages).
"Final Office Action," for U.S. Appl. No. 14/883,895 dated Sep. 14, 2018 (16 pages).
"Final Office Action," for U.S. Appl. No. 15/787,985 dated Jan. 17, 2020 (16 pages).
"Final Office Action," for U.S. Appl. No. 16/280,644 dated Mar. 30, 2021 (17 pages).
"Final Office Action," for U.S. Appl. No. 16/656,159 dated Mar. 3, 2022 (17 pages).
"First Office Action," for Chinese Patent Application No. 201580056417.2 dated Feb. 11, 2019 (13 pages) with English summary.
"International Preliminary Report on Patentability," for PCT Application No. PCT/US2015/056243 dated May 4, 2017 (8 pages).
"International Preliminary Report on Patentability," for PCT Application No. PCT/US2017/057318 dated May 2, 2019 (11 pages).
"International Preliminary Report on Patentability," for PCT Application No. PCT/US2018/033166 dated Nov. 28, 2019 (8 pages).
"International Preliminary Report on Patentability," for PCT Application No. PCT/US2018/037144 dated Dec. 27, 2018 (7 pages).
"International Preliminary Report on Patentability," for PCT Application No. PCT/US2019/056766 dated Apr. 29, 2021 (10 pages).
"International Preliminary Report on Patentability," for PCT Application No. PCT/US2019/081744 dated Sep. 3, 2020 (11 pages).
"International Preliminary Report on Patentability," for PCT Application No. PCT/US2020/030223 dated Nov. 11, 2021 (11 pages).
"International Search Report and Written Opinion," for PCT Application No. PCT/US2015/056243 dated Jan. 26, 2016 (12 pages).
"International Search Report and Written Opinion," for PCT Application No. PCT/US2017/037144 dated Oct. 6, 2017 (11 pages).
"International Search Report and Written Opinion," for PCT Application No. PCT/US2017/057318 dated Feb. 6, 2018 (14 pages).
"International Search Report and Written Opinion," for PCT Application No. PCT/US2018/033166 dated Oct. 2, 2018 (12 pages).
"International Search Report and Written Opinion," for PCT Application No. PCT/US2019/056766 dated Mar. 17, 2020.
"International Search Report and Written Opinion," for PCT Application No. PCT/US2019/081744 dated Jun. 28, 2019 (16 pages).
"International Search Report and Written Opinion," for PCT Application No. PCT/US2020/030223 dated Jul. 27, 2020 (17 pages).
"Invitation to Pay Additional Fees and, Where Applicable, Protest Fee," for PCT Application No. PCT/US2019/018744 dated May 7, 2019 (11 pages).
"Mechanical Data," Dgs (S-PDSO-G10) DSC0010B Package Outline, Example Board Layout, and Stencil Design. Texas Instruments 2016 (5 pages).

"NANO Mobile Healthcare Inc.," Company Profile on Reuters.com URL <http://www.reuters.com/finance/stocks/companyProfile?symbol=VNTH.PK> accessed Mar. 17, 2017 (2 pages).
"Non-Final Office Action," for U.S. Appl. No. 14/883,895 dated Apr. 30, 2018 (37 pages).
"Non-Final Office Action," for U.S. Appl. No. 14/883,895 dated Feb. 15, 2019 (17 pages).
"Non-Final Office Action," for U.S. Appl. No. 15/787,985 dated Oct. 10, 2019 (40 pages).
"Non-Final Office Action," for U.S. Appl. No. 15/982,506 dated Dec. 11, 2019 (41 pages).
"Non-Final Office Action," for U.S. Appl. No. 16/280,644 dated Feb. 24, 2021 (46 pages).
"Non-Final Office Action," for U.S. Appl. No. 16/656,159 dated Oct. 18, 2021 (52 pages).
"Notice of Allowance," for U.S. Appl. No. 16/280,644 dated Jul. 2, 2021 (8 pages).
"Notice of Allowance," for U.S. Appl. No. 16/656,159 dated May 13, 2022 (11 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
"Partial File History," for U.S. Appl. No. 14/883,895 dated Nov. 15, 2015 to Feb. 5, 2020 (284 pages).
"Researchers Identify Inflammatory Biomarkers Indicating Brain Injury," University of Birmingham, posted Jul. 10, 2017 <https://www.birmingham.ac.uk/news/latest/2017/07/researchers-identify-inflammatory-biomarkers-indicating-brain-injury.aspx> (4 pages).
"Response to Advisory Action," dated Dec. 3, 2018, for U.S. Appl. No. 14/883,895, submitted via EFS-Web on Dec. 14, 2018, 11 pages.
"Response to Communication Pursuant to Article 94(3) EPC," for European Patent Application No. 18180455.0 filed Jun. 6, 2019 (44 pages).
"Response to Communication Pursuant to Article 94(3) EPC," for European Patent Application No. 18180455.0 filed Nov. 12, 2019 (9 pages).
"Response to Communication Pursuant to Article 94(3) EPC," for European Patent Application No. 19711730.2 filed Dec. 8, 2021 (8 pages).
"Response to Communication Pursuant to Rules 161(1) and 162 EPC," for European Patent Application No. 15790739.5 filed with the EPO Dec. 8, 2017 (14 pages).
"Response to Communication Pursuant to Rules 161(1) and 162 EPC," for European Patent Application No. 17733246.7 filed May 29, 2019 (22 pages).
"Response to Communication Pursuant to Rules 161(1) and 162 EPC," for European Patent Application No. 17794832.0 filed Dec. 6, 2019 (9 pages).
"Response to Communication pursuant to Rules 161(1) and 162 EPC," for European Patent Application No. 19711730.2 filed Apr. 12, 2021 (9 pages).
"Response to Communication Pursuant to Rules 161(1) and 162 EPC," for European Patent Application No. 19798812.4 filed Dec. 8, 2021 (10 pages).
"Response to Communication Pursuant to Rules 161(1) and 162 EPC," for European Patent Application No. 20725391.5 filed Jun. 9, 2022 (13 pages).
"Response to Final Rejection," dated Mar. 3, 2022 for U.S. Appl. No. 16/656,159, submitted via EFS-Web on May 3, 2022, 11 pages.
"Response to Final Rejection," dated Mar. 30, 2021 for U.S. Appl. No. 16/280,644, submitted via EFS-Web on Jun. 18, 2021, 7 pages.
"Response to Final Rejection," dated Sep. 14, 2018, for U.S. Appl. No. 14/883,895, submitted via EFS-Web on Nov. 7, 2018, 11 pages.
"Response to Non-Final Office Action," for U.S. Appl. No. 14/883,895 dated Apr. 30, 2018 and filed with the USPTO Jul. 2, 2018 (18 pages).
"Response to Non-Final Rejection," dated Feb. 24, 2021 for U.S. Appl. No. 16/280,644, submitted via EFS-Web on Mar. 18, 2021, 9 pages.

(56) References Cited

OTHER PUBLICATIONS

"Response to Non-Final Rejection," dated Oct. 10, 2019 for U.S. Appl. No. 15/787,985, submitted via EFS-Web on Jan. 7, 2020, 17 pages.
"Response to Non-Final Rejection," dated Oct. 18, 2021 for U.S. Appl. No. 16/656,159, submitted via EFS-Web on Jan. 18, 2022, 15 pages.
"Standard Terms and Conditions for Evaluation Modules," Texas Instruments 2016 (5 pages).
Arasaradnam, R. P., et al. "Review Article: Next Generation Diagnostic Modalities in Gastroenterology-Gas Phase Volatile compound biomarker detection," Alimentary Pharmacology and Therapeutics 2014; 39: 780-789 (10 pages).
Banoei, Mohammad Mehdi, et al. "Metabolomics and Biomarker Discovery in Traumatic Brain Injury," Journal of Neurotrauma, vol. 35, No. 16, Mar. 2018 (59 pages).
Boots, Agnes W., et al. "The Versatile Use of Exhaled Volatile Organic Compounds in Human Health and Disease," J. Breath Res. 6 (2012) 027108 (21 pages).
Chen, Liangyou, et al. "Diagnosis of Hemorrhage in a Prehospital Trauma Population Using Linear and Nonlinear Multiparameter Analysis of Vital Signs," 2007 Annual International Conference of the IEEE Engineering and Medicine and Biology Society, Aug. 22, 2007 (4 pages).
Chinopoulos, Christos "Which way Does the Citric Acid Cycle Turn During Hypoxia? The Critical Role of a-Ketoglutarate Dehydrogenase Complex," Journal of Neuroscience Research 91:1030-1043 (2013), 14 pages.
Chouchani, Edward T., et al. "Ischaemic Accumulation of Succinate Controls Reperfusion Injury Through Mitochondrial ROS," Nature. 2014; 515 (7527):431-435 (author manuscript), 29 pages.
D'Alessandro, Angelo, et al. "Early Hemorrhage Triggers Metabolic Responses That Build Up During Prolonged Shock," Am J Physiol Regul Integr Comp Physiol 308: R1034-R1044, 2015 (11 pages).
D'Alessandro, Angelo, et al. "Plasma Succinate is a Predictor of Mortality in Critically Injured Patients," Journal of Trauma and Acute Care Surgery. 2017;83(3):491-495, Author manuscript (9 pages).
D'Alessandro, Angelo, et al. "Trauma/Hemorrhagic Shock Instigates Aberrant Metabolic Flux Through Glycolytic Pathways, as Revealed by Preliminary C-glucose Labeling Metabolomics," Journal of Translational Medicine 2015;13(1): 253 (14 pages).
Deen, David A., et al. "Graphene-Based Quantum Capacitance Wireless Vapor Sensors," IEEE Sensors Journal, vol. 14, No. 5, May 2014, pp. 1459-1466 (8 pages).
Droscher, S., et al. "Quantum Capacitance and Density of States of Graphene," Phys. Scr. T146 (2012) 014009, pp. 1-5 (5 pages).
Ebrish, M. A., et al. "Dielectric Thickness Dependence of Quantum Capacitance in Graphene Varactors with Local Metal Back Gates," Device Research Conference, 2012 (2 pages).
Ebrish, M. A., et al. "Operation of Multi-Finger Graphene Quantum Capacitance Varactors using Planarized Local Bottom Gate Electrodes," Applied Physics Letters, vol. 100, No. 14, Apr. 2012 (4 pages).
Ebrish, Mona A., et al. "Effect of Noncovalent Basal Plane Functionalization of the Quantum Capacitance in Graphene," ACS Appl. Mater. Interfaces 2014, 6, 10296-10303 (8 pages).
El Sayad, Mohamed, et al. "Recent Advances of Hemorrhage Management in Severe Trauma," Emergency Medicine International, vol. 2014, Article ID 635956 (5 pages).
Emam, Shadi, et al. "A Molecularly Imprinted Electrochemical Gas Sensor to Sense Butylated Hydroxytoluene in Air," Journal of Sensors, vol. 18, article ID 3437149, May 9, 2018, pp. 1-9 (10 pages).
Fisher, James P., et al. "Central Sympathetic Overactivity: Maladies and Mechanisms," Autonomic Neuroscience 148.1 (2009): 5-15 (11 pages).
Georgakilas, Vasilios, et al. "Functionalization of Graphene: Covalent and Non-Covalent Approaches, Derivatives and Applications," Chemical Reviews, 2012, 14:112(11), pp. 6156-6214.
Goolsby, Craig, et al. "Just-in-Time to Save Lives: A Pilot Study of Layperson Tourniquet Application," Academic Emergency Medicine, 2015;22(9):1113-1117 (5 pages).
Gutierrez, Guillermo, et al. "Clinical Review: Hemorrhagic Shock," Critical Care 2004, 8:373-381 (9 pages).
Hill, Lisa J., et al. "Cystain D (CST5): An Ultra-Early Inflammatory Biomarker of Traumatic Brain Injury," Sci Rep. Jul. 10, 2017;7(1):5002 (10 pages).
Howard, JT, et al. "Reexamination of a Battlefield Trauma Golden Hour Policy," Journal of Trauma and Acute Care Surgery 2018;84(1): 11-18, Abstract only (2 pages).
Hu, Yuhai, et al. "Chemically Functionalized Graphene and Their Applications in Electrochemical Energy Conversion and Storage," Advances in Graphene Science, Chapter 7, 2013, pp. 161-190 (30 pages).
Kauvar, David S., et al. "Impact of Hemorrhage on Trauma Outcome: An Overview of Epidemiology, Clinical Presentations, and Therapeutic Considerations," Journal of Trauma and Acute Care Surgery, 2006;60(6): S3-S11 (9 pages).
Koester, Steven J. "High Quality Factor Graphene Varactors for Wireless Sensing Applications," Applied Physics Letters 99, 163105 (2011), 3 pages.
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Kotwal, Russ S., et al. "Eliminating Preventable Death on the Battlefield," Archives of Surgery 2011;146(12): 1350-1358 (9 pages).
Krausz, Michael M. "Initial Resuscitation of Hemorrhagic Shock," World Journal of Emergency Surgery 2006, 1:14 (5 pages).
Lexcen, D. R., et al. "Metabolomics Classifies Phase of Care and Identifies Risk for Mortality in a Porcine Model of Multiple Injuries and Hemorrhagic Shock," Journal of Trauma and Acute Care Surgery 2012;73(2):S147-S155, Abstract only (2 pages).
Li, Xiao, et al. "Digital Health: Tracking Physiomes and Activity Using Wearable Biosensors Reveals Useful Health-Related Information," PLoS Biology 15.1 (2017): e2001402 (30 pages).
Lusczek, Elizabeth R., et al. "Assessment of Key Plasma Metabolites in Combat Casualties," Journal of Trauma and Acute Care Surgery. 2017;82(2):309-316 (8 pages).
Ma, Rui, et al. "Acetone Sensing Using Graphene Quantum Capacitance Varactors," 2016 IEEE Sensors, Orlando, FL, 2016 (3 pages).
Magera, Mark J., et al. "Methylmalonic Acid Measured in Plasma and Urine by Stable-Isotope Dilution and Electrospray Tandem Mass Spectrometry," Clin Chem. Nov. 2000;46(11):1804-10 (7 pages).
Murphy, Michael P., et al. "Krebs Cycle Reimagined: The Emerging Roles of Succinate and Itaconate as Signal Transducers," Cell, vol. 174, Issue 4, Aug. 9, 2018, pp. 780-784 (5 pages).
Nakhleh, Morad K., et al. "Diagnosis and Classification of 17 Diseases from 1404 Subjects via Pattern Analysis of Exhaled Molecules," ACS Nano 2017, 11, 112-125 (14 pages).
Navaneethan, Udayakumar, et al. "Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).
Olson, Eric J, et al. "Capacitive Sensing of Intercalated H2O Molecules Using Graphene," ACS Appl. Mater. Interfaces 2015, 7(46), 25804-25812 (29 pages).
Oprea, A., et al. "Integrated Temperature, Humidity and Gas Sensors on Flexible Substrates for Low-Power Applications," 007 IEEE Sensors, Atlanta, GA, 2007, pp. 158-161 (4 pages).
Rassaei, Liza, et al. "Lactate Biosensors: Current Status and Outlook," Anal Bioanal Chem (2014) 406:123-137 (16 pages).
Russo, Matthew V., et al. "Inflammatory Neuroprotection Following Traumatic Brain Injury," Science. Aug. 19, 2016;353(6301):783-5 (4 pages).
Slaughter, Anne L., et al. "Glutamine Metabolism Drives Succinate Accumulation in Plasma and the Lung During Hemorrhagic Shock," Journal of Trauma and Acute Care Surgery. 2016;81(6):1012-1019 (8 pages).

(56) References Cited

OTHER PUBLICATIONS

Stewart, Ian J., et al. "The Potential Utility of Urinary Biomarkers for Risk Prediction in Combat Casualties: A Prospective Observational Cohort Study," Critical Care 2015;19(1):252 (8 pages).

Tripathi, Kumud Malika, et al. "Recent Advances in Engineered Graphene and Composites for Detection of Volatile Organic Compounds (VOCs) and Non- Invasive Diseases Diagnosis," Carbon 110 (2016)97-129 (34 pages).

Umbrello, Michele, et al. "The Key Role of Nitric Oxide in Hypoxia: Hypoxic Vasodilation and Energy Supply-Demand Matching," Antioxidants and Redox Signaling, vol. 19, No. 14, Nov. 10, 2013 (22 pages).

Wang, David "FDC1004: Basics of Capacitive Sensing and Applications," Application Report SNOA927, Texas Instruments Dec. 2014 (12 pages).

Witowski, Nancy E., et al. "Metabolomic Analysis of Survival in Carbohydrate Pre-Fed Pigs Subjected to Shock and Polytrauma," Molecular BioSystems Apr. 26, 2016; 12(5), 34 pages.

Woodcock, Thomas, et al. "The Role of Markers of Inflammation in Traumatic Brain Injury," Front Neurol. Mar. 4, 2013;4:18 (18 pages).

Zhang, Yao, et al. "Capacitive Sensing of Glucose in Electrolytes using Graphene Quantum Capacitance Varactors," ACS Appl. Mater. Interfaces 2017, 9, 38863-38869 (7 pages).

Zhen, Xue, et al. "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).

"Final Office Action," for U.S. Appl. No. 16/860,529 dated Jun. 23, 2023 (21 pages).

"Non-Final Office Action," for U.S. Appl. No. 17/520,339 dated Jun. 27, 2023 (49 pages).

"Final Office Action," for U.S. Appl. No. 17/520,339 dated Oct. 10, 2023 (18 pages).

"First Office Action," for Chinese Patent Application No. 201980068940.5dated Sep. 19, 2023 (8 pages) with English Summary.

"Response to Final Rejection," dated Jun. 23, 2023, for U.S. Appl. No. 16/860,529, submitted via EFS-Web on Sep. 25, 2023, 10 pages.

"Response to Non-Final Rejection," dated Jun. 27, 2023, for U.S. Appl. No. 17/520,339, submitted via EFS-Web on Sep. 27, 2023, 10 pages.

"Second Office Action," for Chinese Patent Application No. 201980014220.0dated Sep. 4, 2023 (11 pages) with English Summary.

"First Office Action," for Chinese Patent Application No. 202080031802.2 dated Nov. 16, 2023 (6 pages).

\* cited by examiner

SYSTEMS AND METHODS FOR DETECTING A BRAIN CONDITION

This application is a continuation of U.S. application Ser. No. 16/656,159, filed Oct. 17, 2019 and now U.S. Pat. No. 11,442,056, and claims the benefit of U.S. Provisional Application No. 62/747,939, filed Oct. 19, 2018, the content of which is herein incorporated by reference in its entirety.

FIELD

Embodiments herein relate to systems and methods for detecting a brain condition. More specifically, the embodiments herein relate to systems and methods for detecting a brain condition in a subject by analyzing an exhaled breath sample.

BACKGROUND

The accurate and rapid detection of a brain condition can lead to a more rapid and appropriate course of treatment for a subject. For example, the accurate and rapid detection of an injury to the head or the onset of a brain disease or disorder can allow for early application of appropriate treatment and/or preventative measures to provide the maximum benefit for the subject.

However, current detection methods for brain conditions have various drawbacks. Some detection methods may require a subject to be present at a clinic or other care facility for blood draws, imaging, and diagnosis. Some detection methods may not provide useful information until after significant damage to and/or impairment of the individual has already taken place.

SUMMARY

In a first aspect, a method for detecting a brain condition in a subject is included. The method can include obtaining a breath sample from the subject and contacting it with a chemical sensor element, where the chemical sensor element includes a plurality of discrete graphene varactors. The method can include sensing and storing capacitance of the discrete graphene varactors to obtain a sample data set and classifying the sample data set into one or more preestablished brain condition classifications.

In a second aspect, in addition to one or more of the preceding or following aspects, or in the alternative to some aspects, the brain condition can include a brain injury.

In a third aspect, in addition to one or more of the preceding or following aspects, or in the alternative to some aspects, the brain injury can include a traumatic brain injury.

In a fourth aspect, in addition to one or more of the preceding or following aspects, or in the alternative to some aspects, the brain injury can include an ischemic brain injury.

In a fifth aspect, in addition to one or more of the preceding or following aspects, or in the alternative to some aspects, obtaining a breath sample from the subject can include obtaining a breath sample within 10 minutes following the brain injury.

In a sixth aspect, in addition to one or more of the preceding or following aspects, or in the alternative to some aspects, obtaining a breath sample from the subject can include obtaining a breath sample at least two times over a period of 24 hours following an onset of the brain injury.

In a seventh aspect, in addition to one or more of the preceding or following aspects, or in the alternative to some aspects, the sample data set can be further analyzed to determine an improvement or a worsening in the brain condition of the subject over 24 hours.

In an eighth aspect, in addition to one or more of the preceding or following aspects, or in the alternative to some aspects, the brain condition can be at least one of a chronic condition, a subacute condition, and an acute condition.

In a ninth aspect, in addition to one or more of the preceding or following aspects, or in the alternative to some aspects, obtaining a breath sample from the subject can be performed prior to the subject participating in a sporting event.

In a tenth aspect, in addition to one or more of the preceding or following aspects, or in the alternative to some aspects, obtaining a breath sample from the subject can be performed prior to the subject participating in a sporting event and is performed at least one addition time after the sporting event begins or is completed.

In an eleventh aspect, in addition to one or more of the preceding or following aspects, or in the alternative to some aspects, sensing and storing capacitance of the graphene varactors to obtain a sample data set can be performed across a range of bias voltages.

In a twelfth aspect, in addition to one or more of the preceding or following aspects, or in the alternative to some aspects, the bias voltage is from −3 V to 3 V.

In a thirteenth aspect, in addition to one or more of the preceding or following aspects, or in the alternative to some aspects, at least 40 discrete capacitance values are stored for each graphene varactor across the range of bias voltages.

In a fourteenth aspect, in addition to one or more of the preceding or following aspects, or in the alternative to some aspects, volatile organic compounds (VOCs) from the exhaled breath sample interface with the discrete graphene varactors to influence sensed capacitance.

In a fifteenth aspect, in addition to one or more of the preceding or following aspects, or in the alternative to some aspects, the plurality of discrete graphene varactors can be functionalized with polar compounds having a dipole moment from 1.5 D to 5 D.

In a sixteenth aspect, in addition to one or more of the preceding or following aspects, or in the alternative to some aspects, the method can include storing additional data regarding the subject beyond sensed capacitance as part of the sample data set that is classified.

In a seventeenth aspect, in addition to one or more of the preceding or following aspects, or in the alternative to some aspects, the additional data can include at least one of prior traumatic brain injuries of the subject; the time elapsed since an event has occurred which resulted in an injury to the subject; age of the subject; results of a neurological examination; symptoms experienced by the subject; and data regarding specific biomarkers of a brain condition.

In an eighteenth aspect, in addition to one or more of the preceding or following aspects, or in the alternative to some aspects, the one or more preestablished brain condition classifications can include traumatic brain injury, ischemic brain injury, neurodegenerative brain disorders, autoimmune brain disorders, psychiatric disorders, or developmental disorders.

In a nineteenth aspect, in addition to one or more of the preceding or following aspects, or in the alternative to some aspects, the sample data set is further analyzed to identify if the subject is a candidate for drug therapy for the brain condition.

In a twentieth aspect, in addition to one or more of the preceding or following aspects, or in the alternative to some aspects, a method of treating a brain condition in a subject is included. The method can include obtaining an exhaled breath sample from the subject and contacting it with a chemical sensor element, where the chemical sensor element includes a plurality of discrete graphene varactors. The method can include sensing and storing capacitance of the discrete graphene varactors to obtain a sample data set and classifying the sample data set into one or more preestablished brain condition classifications. The method can include treating the patient based on the brain condition classification.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

An injury to the head or the onset of a brain disease or disorder can result in an increase and/or decrease of various volatile organic compounds (VOCs) within the breath of a subject. Thus, detection of VOCs and/or patterns related to the same within the breath of a subject can be of substantial diagnostic value to help provide appropriate care and/or treatment to a subject after sustaining an injury to the head or after onset of a diseased state. In some cases, VOCs and/or patterns regarding the same can be detected within minutes of an injury occurring.

In accordance with embodiments herein, various volatile organic compounds (VOCs) can be detected within the breath of a subject to aid in the diagnosis of a brain condition (such as a brain injury, disease or disorder) and/or as a part of methods of treating or caring for the same. In various embodiments, analysis of VOCs can be performed rapidly in the field, beyond just in a care facility. Thus, various embodiments herein can provide the opportunity to detect an injury to the head or a diseased state in the most rapid way possible.

In some embodiments, detection of VOCs and/or patterns related to the same for a period of time following onset of injury or disease can be used to monitor progress in response to a treatment or to alter a course of treatment as needed.

Figure 1:
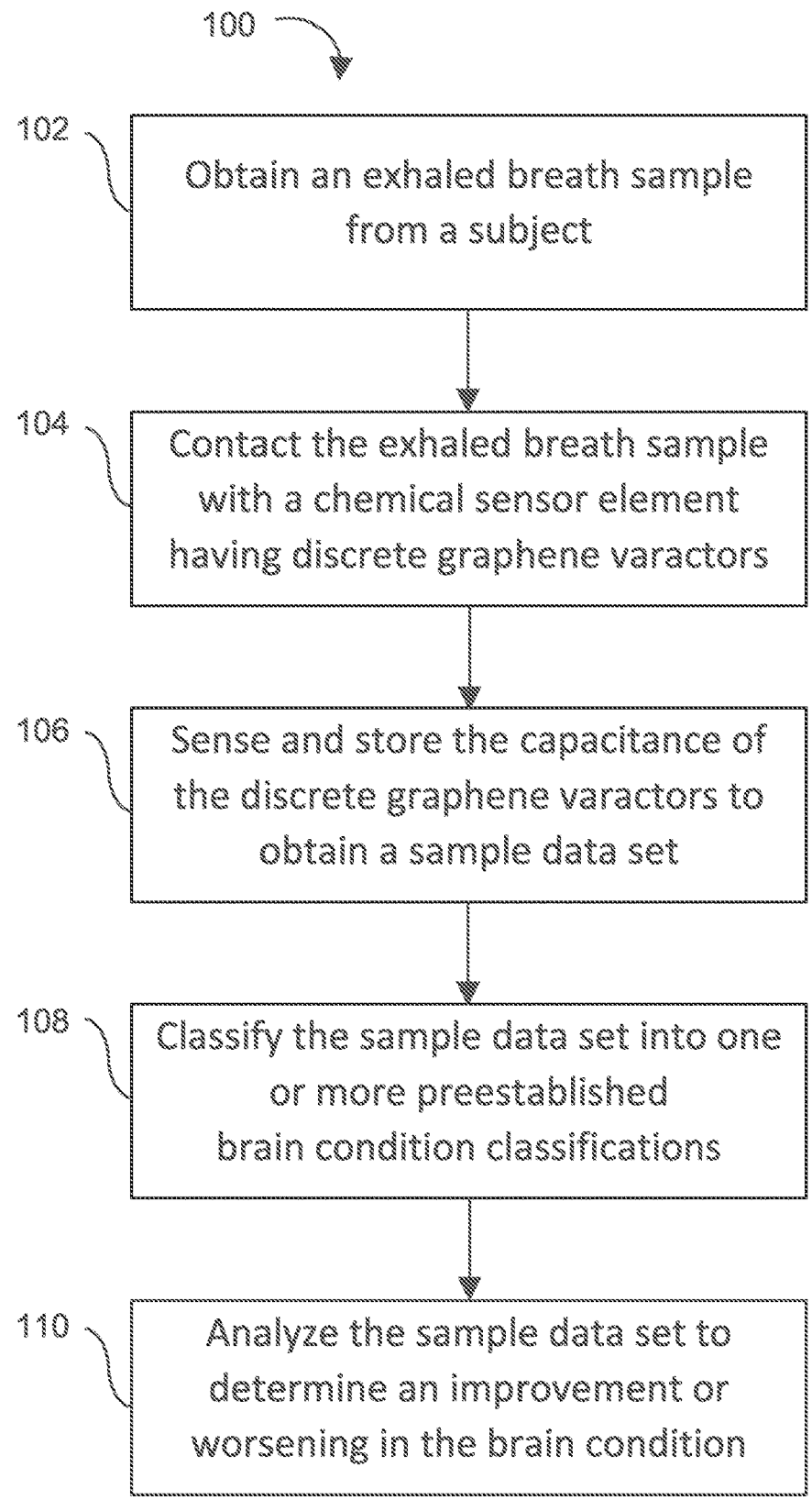
FIG. 1 is a schematic view of a method for detecting a brain condition in a subject in accordance with various embodiments herein.

Referring now to FIG. 1, a schematic view of a method 100 for detecting a brain condition in a subject is shown in accordance with various embodiments herein. The method 100 for detecting a brain condition can include obtaining an exhaled breath sample from the subject at 102 and contacting it with a chemical sensor element at 104. The chemical sensor element can include a plurality of discrete graphene varactors (that will be discussed below in reference to FIGS. 5-10). In some embodiments, the step of obtaining an exhaled breath sample from a subject can include obtaining a breath sample within 10 minutes following the brain injury. In other embodiments, the step of obtaining an exhaled breath sample from the subject comprises obtaining a breath sample at least two times over a period of 24 hours following an onset of the brain injury. In some embodiments the subject is a human. In other embodiments, the subject is an animal, including, but not to be limited to, a cow, bison, pig, sheep, goat, horse, dog, cat, and chicken.

The step of obtaining a breath sample of a subject can be performed multiple times over a course of monitoring a patient after an injury to the head. A breath sample can be obtained at various time points following the onset of an injury to the head. The time points can include, but not be limited to immediately after the injury to the head, within 10 minutes following a brain injury, within 60 minutes following a brain injury, and within 2 hours following a brain injury. A breath sample can be obtained at additional time points, including at 5, minutes, 10 minutes, 20 minutes, 30 minutes, 40 minutes, 50 minutes, 1 hour, 1.5 hours, 2 hours, 2.5 hours, 3 hours, 4 hours, 4.5 hours, 5 hours, 6 hours, 7 hours, 8 hours, 9 hours, 10 hours, 11 hours, 12 hours, 18 hours, 24 hours, 48 hours, or at various time points between any of the foregoing. In some embodiments, a breath sample can be obtained at greater than 48 hours.

The method 100 can also include sensing and storing capacitance of the discrete graphene varactors to obtain a sample data set at 106. The method 100 can include classifying the sample data set into one or more preestablished brain condition classifications at 108. The one or more preestablished brain condition classifications will be discussed in more detail below.

In some embodiments, the method 100 can include analyzing the sample data set 110 to determine an improvement or a worsening in the brain condition of the subject over 24 hours. In some embodiments, the method 100 can include analyzing the sample data set 110 to determine an improvement or a worsening in the brain condition of the subject over 48 hours. In other embodiments, the method 100 can include analyzing the sample data set 110 to determine an improvement or a worsening in the brain condition of the subject over 1 week to 2 weeks or more. The sample data set can be further analyzed to identify if the subject is a candidate for rehabilitation treatment or drug therapy for the brain condition.

Sensing and storing capacitance of the graphene varactors to obtain a sample data set can be performed across a range of bias voltages. In some embodiments, the sensing and storing of capacitance of the graphene varactors can include sensing the capacitance from −3 V to 3 V. In some embodiments, the range of bias voltages can be from −2 V to 2 V. In other embodiments, the range of voltages can be from −1.5 V to 1.5 V. In some embodiments, the storing of capacitance of the graphene varactors can include sensing the capacitance at −3 V, −2.5 V, −2.0 V, −1.5 V, −1.0 V, −0.5 V, 0.5 V, 1.0 V, 1.5 V, 2.0 V, 2.5 V, 3.0 V. It will be appreciated that the sensing and storing of capacitance of the graphene varactors can include sensing the capacitance within a range, wherein any of the forgoing voltages can serve as the lower or upper bound of the range, provided that the lower bound of the range is a value less than the upper bound of the range.

The sensing and storing of capacitance of the graphene varactors across a range of bias voltages can include sensing the capacitance in a stepped fashion. Sensing and storing of capacitance in a stepped fashion can be performed at voltage intervals, such as every 5, 10, 25, 50, 75, 100, 125, 150, 200, 300, 400, or 500 mV, or by a stepped amount falling within a range between any of the foregoing.

When sensing and storing of capacitance of the graphene varactors across a range of bias voltages in a stepped fashion, a sample data set can be obtained at each bias voltage for each discrete graphene varactor. The sensing and storing of capacitance of the graphene varactors across a range of bias voltages to obtain a sample data set can include storing at least 10, 20, 30, 40, 50, 60, 70, 80, 90, 100, 125, 150, 175, 200, 250, 300, 350, 400, 450, or 500 discrete capacitance values (or a number of discrete capacitance values falling within a range between any of the foregoing) for each graphene varactor across the range of bias voltages.

The methods herein can also include gathering and/or storing additional data regarding the subject beyond sensed capacitance as part of the sample data set that is classified. The additional data can include, but not be limited to prior traumatic brain injuries of the subject; the time elapsed since an event has occurred which resulted in an injury to the subject; age of the subject; results of a neurological examination; symptoms experienced by the subject; and data regarding specific biomarkers of a brain condition. The additional data can also include information regarding past treatment regimens, and successes or failures of past treatment regimens.

It will be appreciated that volatile organic compounds (VOCs) from the exhaled breath sample of a subject can interface with the discrete graphene varactors to influence sensed capacitance. The VOCs in a subject's exhaled breath before an injury to the head can be different than the VOCs in a subject's exhaled breath after an injury. One or more exhaled breath samples can be obtained from a subject prior to an injury to the head during a training regimen. The data obtained from sensing and storing capacitance from the exhaled breath of an uninjured subject can serve as a baseline value for a non-injured state. Examples of obtaining an exhaled breath sample from a subject in an uninjured state can include, but should not be limited to, obtaining a breath sample during a preseason athletic training schedule, obtaining a breath sample during a basic military training schedule, or obtaining a breath sample during an employment training schedule on a daily, weekly, or monthly basis. In some embodiments, data from exhaled breath can be obtained from a subject in a clinical setting as part of a routine physical examination and can serve as a baseline for the VOC content in that patient's breath should an injury to the head or brain disorder occur at some point in the future.

Figure 2:
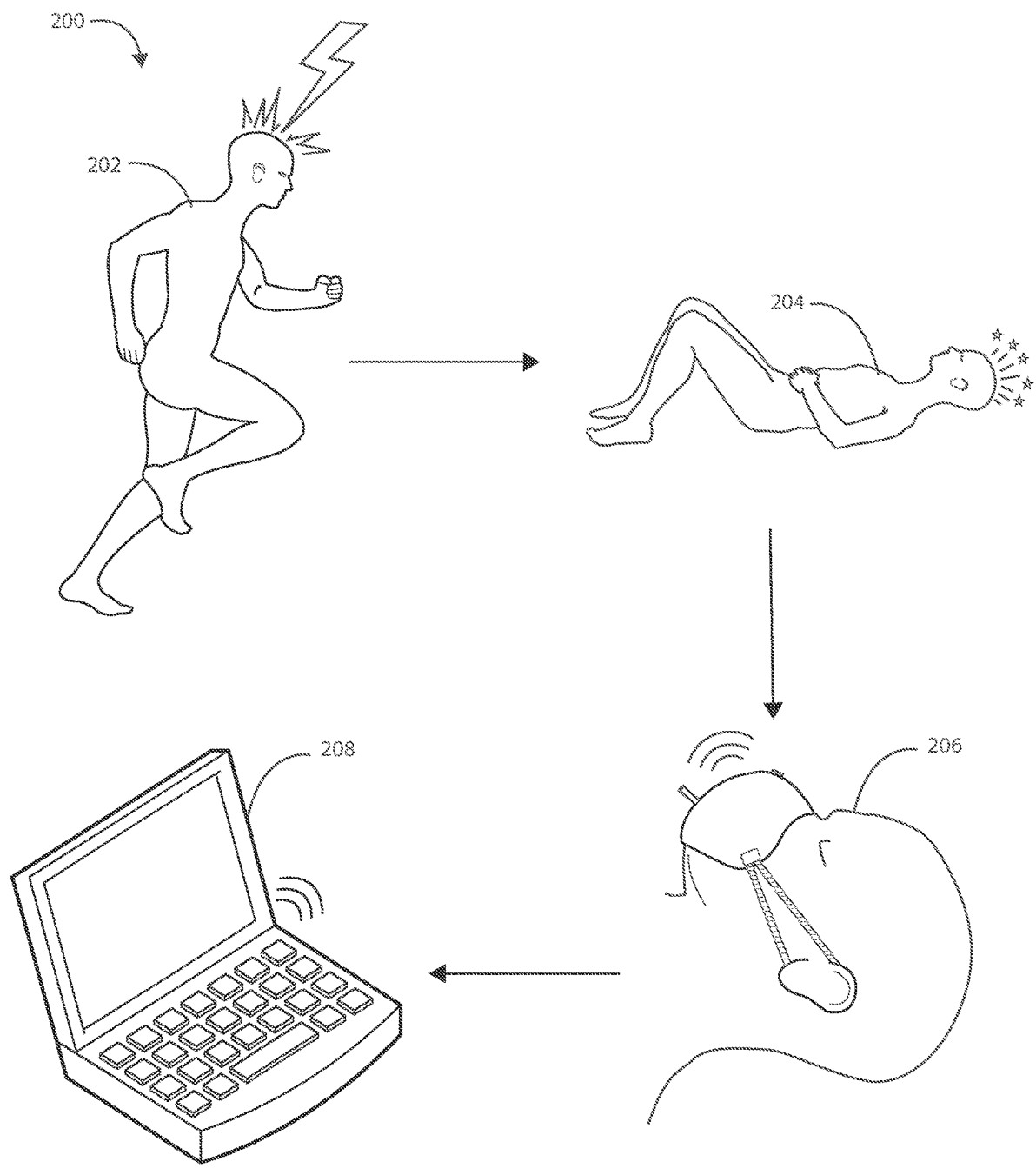
FIG. 2 is a schematic view of a method for detecting a brain condition in a subject in accordance with various embodiments herein.

During physical activity in a sporting event, a military deployment, a work environment, or the like, a subject can experience an injury to the head that can induce a brain condition in the subject. Having the ability to assess a subject at the site of the injury can be key to providing a rapid diagnosis and appropriate care as soon after the injury event as possible. By way of example, referring now to FIG. 2, a schematic view of a method 200 for detecting a brain condition in a subject experiencing an injury to the head is shown in accordance with various embodiments herein. In FIG. 2, a subject participating in an athletic event is shown experiencing an injury to the head at 202. As a result of the injury to the head, the subject becomes incapacitated by the injury at 204. An exhaled breath sample is obtained from the subject and is contacted with a chemical sensor element containing a plurality of discrete graphene varactors at 206. Sensing and storing capacitance of the discrete graphene varactors to obtain a sample data set is shown at 208.

Figure 3:
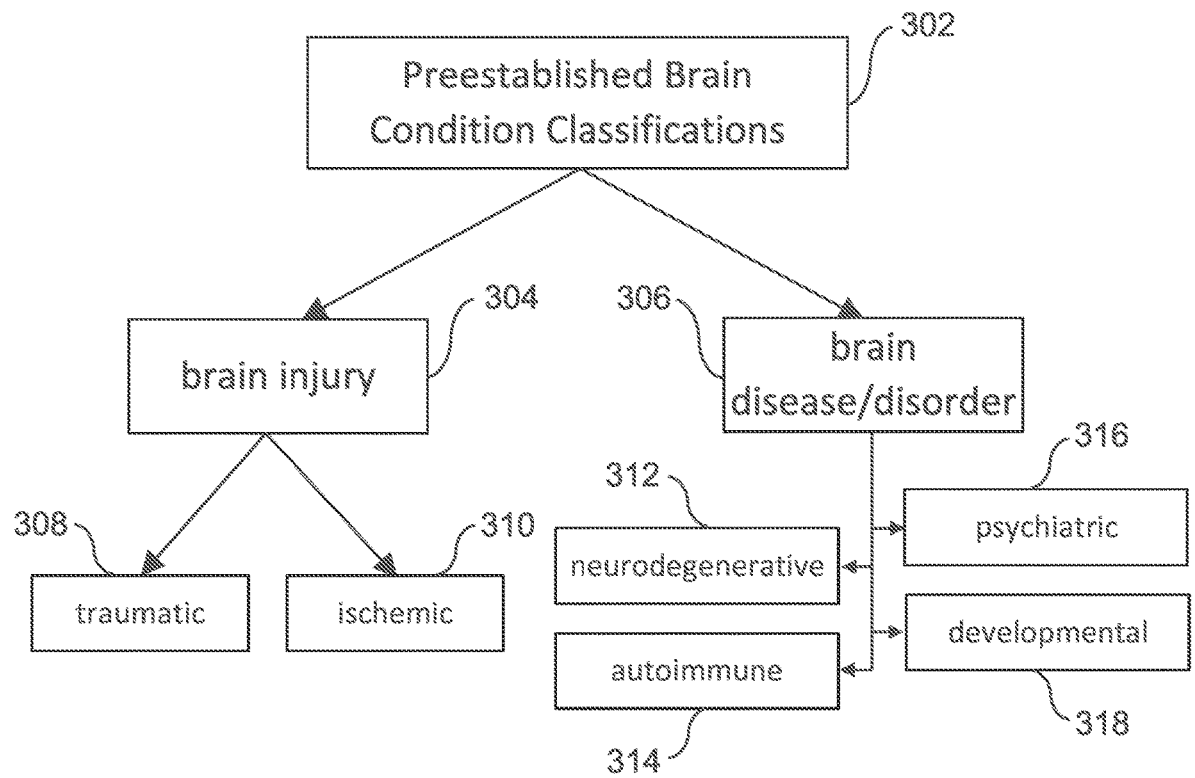
FIG. 3 is a schematic of view of preestablished brain condition classifications in accordance with various embodiments herein.

The types of brain conditions can vary in type, severity, and duration, and can be classified into preestablished brain condition classifications. Referring now to FIG. 3 a schematic of view of preestablished brain condition classifications 302 is shown in accordance with various embodiments herein. In some embodiments, the brain condition can be a brain injury 304 such as a traumatic brain injury 308 or an ischemic brain injury 310. In other embodiments, the brain condition can include a brain disease, or brain disease 306. As used herein, the terms "brain disease" and "brain disorder" are used interchangeably. The brain injury 304 classifications can further include traumatic brain injury 308, ischemic brain injury 310, and the brain disease 306 classification can further include neurodegenerative brain disorders 312, autoimmune brain disorders 314, psychiatric disorders 316, developmental disorders 318, and the like.

Figure 4:
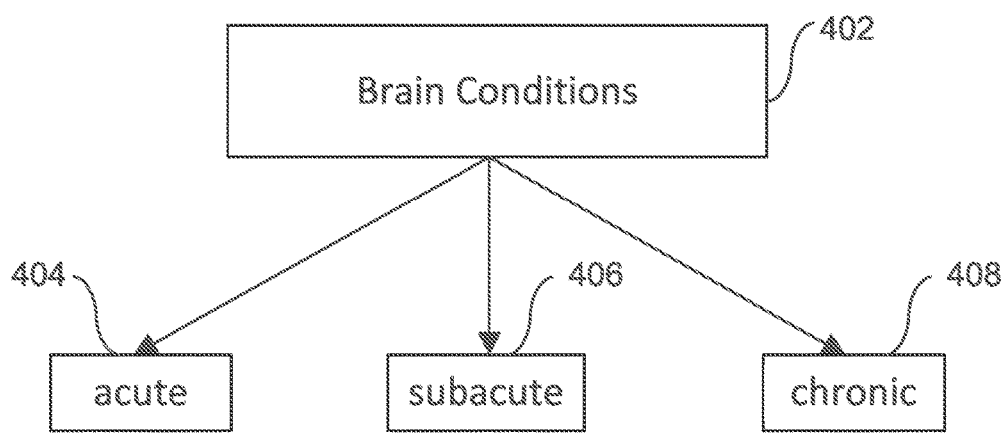
FIG. 4 is a schematic view of brain conditions in accordance with various embodiments herein.

Referring now to FIG. 4 a schematic view of the severity and time of onset for the brain conditions 402 herein is shown in accordance with various embodiments herein. Any of the brain conditions herein can be acute 404, subacute 406, or chronic 408. An acute brain condition can be one that is severe and of rapid onset. A chronic condition can be one that is long to develop and may be severe or non-severe. In some instances, a chronic condition can develop into an acute condition. A subacute condition can fall along a spectrum between an acute condition and a chronic one.

Figure 5:
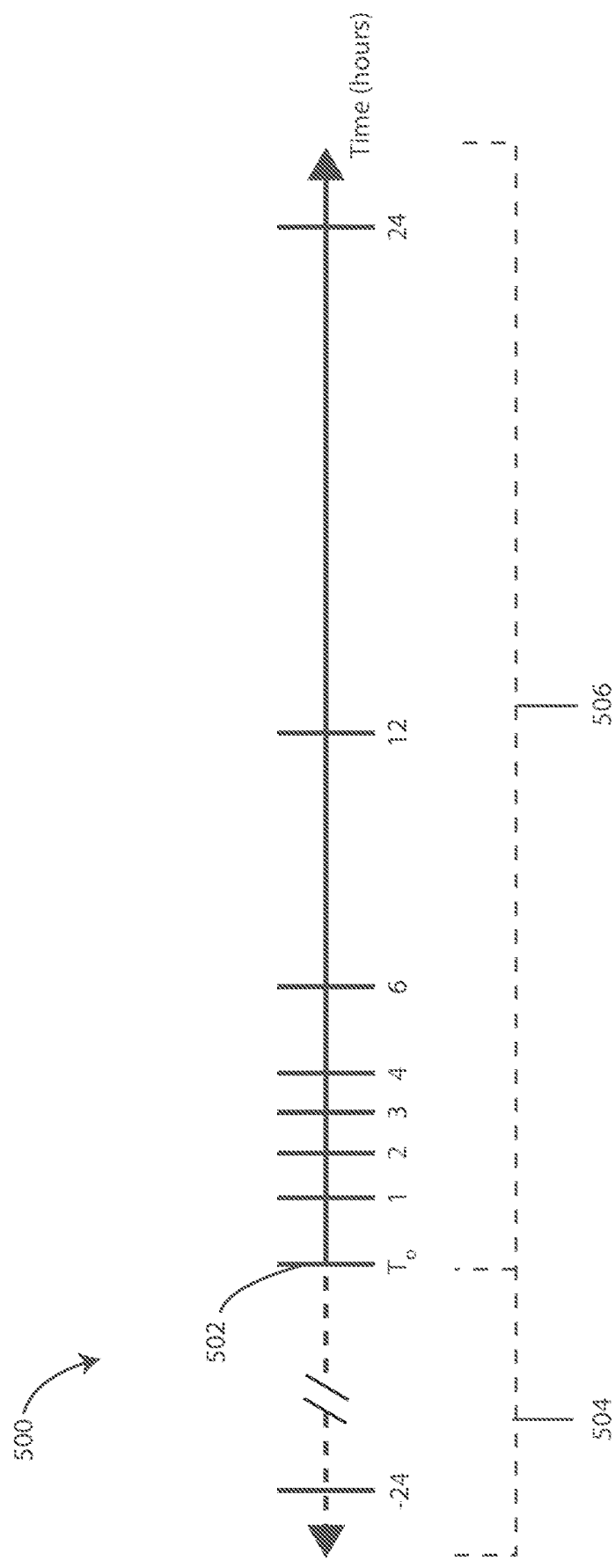
FIG. 5 is a schematic view of a timeline of a method for detecting a brain condition in a subject in accordance with the various embodiments herein.

A timeline can be established to serve as a frame of reference for detecting a brain condition in a subject and for monitoring progression of the subject following onset of a brain condition. Referring now to FIG. 5, a timeline 500 of a method for detecting a brain condition in a subject is shown in accordance with the various embodiments herein. The timeline 500 includes a point at $T_o$, which indicates an event such as an injury to the head or the diagnosis of a brain disease or disorder. The time 504 before an injury to the head or the diagnosis of a brain disease or disorder is to be considered a baseline state for that subject. The time 506 after an injury to the head or the diagnosis of a brain disease or disorder is to be considered reflective of a brain condition in that subject. Timeline 500, shows that an exhaled breath sample can be obtained at a number of time points after an injury to the head, for example, a concussion sustained during a sporting event. In timeline 500, an exhaled breath sample was obtained at 1 hr., 2 hrs., 3 hrs., 4 hrs., 6 hrs., 12 hrs., and 24 hrs. after the heat injury at 502. Data obtained during the time 504 before the head injury to the head can be used to serve as a baseline and can be used to determine the severity of the injury, and the choice of treatment.

In some embodiments, breath testing procedures herein can be performed prior to participation in a sporting event to provide an individual baseline and breath testing can also be performed at least one time after the sporting event begins or is completed and a comparison can be made between the initial value and the one or more later values. In some embodiments, the later testing can be performed after the subject has experienced a blow to the head or otherwise has experienced symptoms such as a headache, blurry/altered vision, dizziness, fallen unconscious or the like. In some embodiments, the later testing can be performed at a defined juncture with respect to the sporting event such as the end of the sporting event, the end of the sporting event season. In some embodiments, the later testing can be performed at a defined time in the future such as days, weeks, months or even years after the initial test. As such, in some embodiments, the subject can be tracked longitudinally. Sporting events herein can include, but are not limited to, football games, hockey games, soccer games, lacrosse games, basketball games, boxing matches, mixed martial arts matches, and the like.

Figure 6:
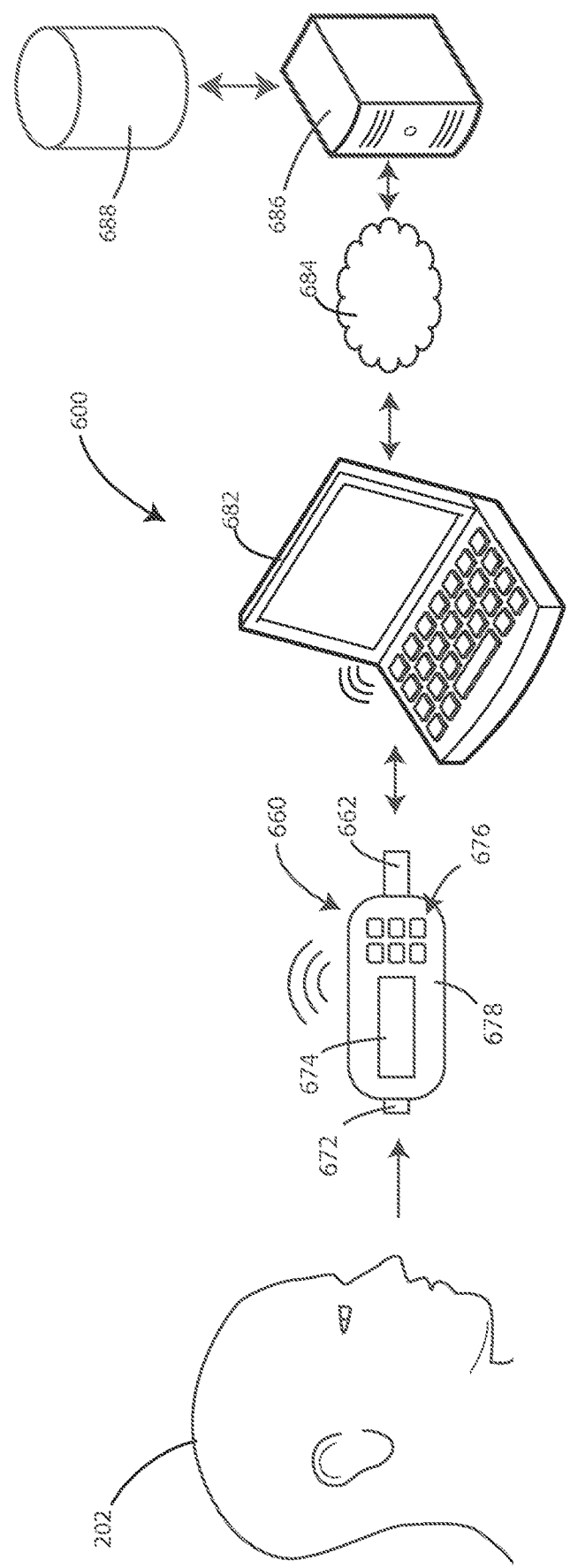
FIG. 6 is a schematic view of various components of a system in accordance with various embodiments herein.

Referring now to FIG. 6, a schematic view is shown of components of a system 600 in accordance with various embodiments herein. The system 600 can include a breath sensing device 660 for sensing volatile organic compounds in an exhaled breath sample of a subject 202 accordance with various embodiments herein. In this embodiment, the system is in a hand-held format that can be used in the field. It will be appreciated, however, that many other formats for the system are contemplated herein.

The breath sensing device 660 can include a housing 678. The breath sensing device 660 can include a mouthpiece 662 into which a subject to be evaluated can blow a breath sample. The breath sensing device 660 can also include a display screen 674 and a user input device 676, such as a keyboard. The breath sensing device 660 can also include a gas outflow port 672. Aspects of breath sensing systems and devices are described in U.S. Publ. Appl. No. 2016/0109440, the content of which is herein incorporated by reference. While FIG. 6 shows a breath sensing device, it will be appreciated that other types of gas sampling systems can also be used herein. For example, gas sampling devices for use with catheters and endoscopy systems can also be used. An exemplary gas sampling device in the context of a catheter or endoscopy device is described in U.S. Pat. No. 11,191,457, the content of which is herein incorporated by reference.

In some embodiments, the system 600 can include a local computing device 682 that can include a microprocessor, input and output circuits, input devices, a visual display, a user interface, and the like. In some embodiments, the breath sensing device 660 can communicate with the local computing device 682 in order to exchange data between the breath sensing device 660 and the local computing device 682. The local computing device 682 can be configured to perform various processing steps with the data received from the breath sensing device 660, including, but not limited to, calculating various parameters described herein. However, it should be appreciated that in some embodiments the features associated with the local computing device 682 can be integrated into the breath sensing device 660. In some embodiments, the local computing device 682 can be a laptop computer, a desktop computer, a server (real or virtual), a purpose dedicated computer device, or a portable computing device (including, but not limited to, a mobile phone, tablet, wearable device, etc.).

The local computing device 682 and/or the breath sensing device 660 can communicate with computing devices in remote locations through a data network 684, such as the Internet or another network for the exchange of data as packets, frames, or otherwise.

In some embodiments, the system 600 can also include a computing device such as a server 686 (real or virtual). In some embodiments, the server 686 can be located remotely from the breath sensing device 660. The server 686 can be in data communication with a database 688. The database 688 can be used to store various patient information, such as that described herein. In some embodiments, the database can specifically include an electronic medical database containing data regarding the health status of a patient, patterns of data associated with various conditions (such as that generated from machine learning analysis of large sets of patient data), demographic data and the like. In some embodiments, the database 688 and/or server 686, or a combination thereof, can store the data generated by the chemical sensor(s) as well as data output generated by machine learning analysis.

Figure 7:
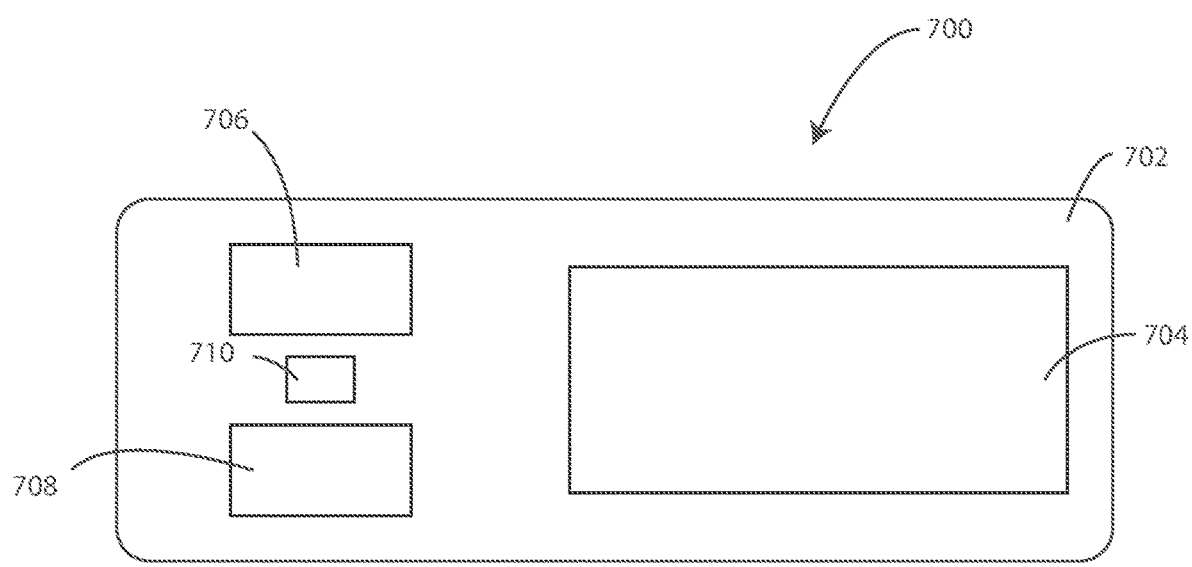
FIG. 7 a schematic top plan view of a chemical sensor element in accordance with various embodiments herein.

Referring now to FIG. 7, a schematic top plan view of a chemical sensor element 700 is shown in accordance with various embodiments herein. The chemical sensor element 700 can include a substrate 702. It will be appreciated that the substrate can be formed from many different materials. By way of example, the substrate can be formed from polymers, metals, glasses, ceramics, cellulosic materials, composites, metal oxides, and the like. The thickness of the substrate can vary. In some embodiments, the substrate has sufficient structural integrity to be handled without undue flexure that could damage components thereon. In some embodiments, the substrate can have a thickness of about 0.05 mm to about 5 mm. The length and width of the substrate can also vary. In some embodiments, the length (or major axis) can be from about 0.2 cm to about 10 cm. In some embodiments, the width (perpendicular to the major axis) can be from about 0.2 cm to about 8 cm. In some embodiments, the chemical sensor element can be disposable. In some embodiments, the chemical sensor element can be reusable.

The chemical sensor element can include a first measurement zone 704 disposed on the substrate 702. In some embodiments, the first measurement zone 704 can define a portion of a first gas flow path. The first measurement zone (or breath sample zone) 704 can include a plurality of discrete graphene varactors that can sense analytes in a gaseous sample, such as a breath sample. A second measurement zone (or environment sample zone), separate from the first measurement zone 704, can also be disposed on the substrate 702. The second measurement zone 706 can also include a plurality of discrete graphene varactors. In some embodiments, the second measurement zone 706 can include the same (in type and/or number) discrete graphene varactors that are within the first measurement zone 704. In some embodiments, the second measurement zone 706 can include only a subset of the discrete graphene varactors that are within the first measurement zone 704. In operation, the data gathered from the first measurement zone, which can be reflective of the gaseous sample analyzed, can be corrected or normalized based on the data gathered from the second measurement zone, which can be reflective of analytes present in the environment. However, in some embodiments, both a first and second measurement zone can reflect the breath sample analyzed. In some embodiments, a second measurement zone is not included.

In some embodiments, a third measurement zone (drift control or witness zone) 708 can also be disposed on the substrate. The third measurement zone 708 can include a plurality of discrete graphene varactors. In some embodiments, the third measurement zone 708 can include the same (in type and/or number) discrete graphene varactors that are within the first measurement zone 704. In some embodiments, the third measurement zone 708 can include only a subset of the discrete graphene varactors that are within the first measurement zone 704. In some embodiments, the third measurement zone 708 can include discrete graphene varactors that are different than those of the first measurement zone 704 and the second measurement zone 706. In some embodiments, a third measurement zone 708 is not included. Aspects of the third measurement zone are described in greater detail below.

The first measurement zone, the second measurement zone, and the third measurement zone can be the same size or can be of different sizes. In some embodiments, the chemical sensor element 700 can also include a component 710 to store reference data. The component 710 to store reference data can be an electronic data storage device, an optical data storage device, a printed data storage device (such as a printed code), or the like. The reference data can include, but is not limited to, data regarding the third measurement zone.

In some embodiments, chemical sensor elements embodied herein can include electrical contacts (not shown) that can be used to provide power to components on the chemical sensor element 700 and/or can be used to read data regarding the measurement zones and/or data from the stored in component 710. However, in other embodiments there are no external electrical contacts on the chemical sensor element 700. Further aspects of exemplary chemical sensor elements can be found in U.S. Pat. No. 11,262,354, the content of which is herein incorporated by reference in its entirety.

Many different types of circuits can be used to gather data from chemical sensor elements. It will be appreciated that the chemical sensor elements embodied herein can include those that are compatible with passive wireless sensing techniques. One example of a passive sensor circuit 1102 and a portion of a reading circuit 1122 is illustrated schematically in FIG. 11 and discussed in more detail below, however, many other circuits are contemplated herein.

Figure 8:
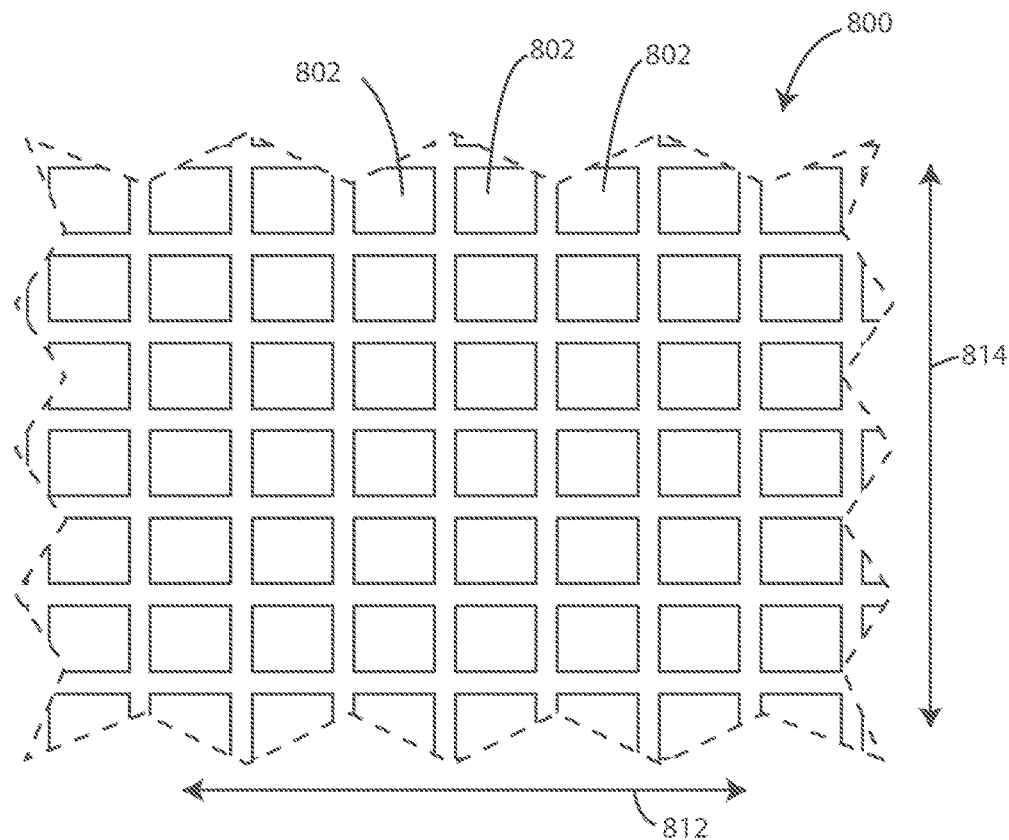
FIG. 8 is a schematic diagram of a portion of a measurement zone in accordance with various embodiments herein.

Referring now to FIG. 8, a schematic diagram of a portion of a measurement zone 800 is shown in accordance with various embodiments herein. A plurality of discrete graphene varactors 802 can be disposed within the measurement zone 800 in an array. In some embodiments, a chemical sensor element can include a plurality of discrete graphene varactors configured in an array within a measurement zone. In some embodiments, the plurality of discrete graphene varactors can be identical, while in other embodiments the plurality of discrete graphene varactors can be different from one another. The discrete graphene varactors herein are described in more detail in U.S. Publ. Appl. No. 2014/0145735, which is herein incorporated by reference in its entirety.

In some embodiments, the discrete graphene varactors can be heterogeneous in that they are all different from one another in terms of their binding behavior or specificity with regard a particular analyte. In some embodiments, some discrete graphene varactors can be duplicated for validation purposes but are otherwise heterogeneous from other discrete graphene varactors. Yet in other embodiments, the discrete graphene varactors can be homogeneous. While the discrete graphene varactors 802 of FIG. 8 are shown as boxes organized into a grid, it will be appreciated that the discrete graphene varactors can take on many different shapes (including, but not limited to, various polygons, circles, ovals, irregular shapes, and the like) and, in turn, the groups of discrete graphene varactors can be arranged into many different patterns (including, but not limited to, star patterns, zig-zag patterns, radial patterns, symbolic patterns, and the like).

In some embodiments, the order of specific discrete graphene varactors 802 across the length 812 and width 814 of the measurement zone can be substantially random. In other embodiments, the order can be specific. For example, in some embodiments, a measurement zone can be ordered so that the specific discrete graphene varactors 802 for analytes having a lower molecular weight are located farther away from the incoming gas flow relative to specific discrete graphene varactors 802 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete graphene varactors.

The number of discrete graphene varactors within a particular measurement zone can be from about 1 to about 100,000. In some embodiments, the number of discrete graphene varactors can be from about 1 to about 10,000. In some embodiments, the number of discrete graphene varactors can be from about 1 to about 1,000. In some embodiments, the number of discrete graphene varactors can be from about 2 to about 500. In some embodiments, the number of discrete graphene varactors can be from about 10 to about 500. In some embodiments, the number of discrete graphene varactors can be from about 50 to about 500. In some embodiments, the number of discrete graphene varactors can be from about 1 to about 250. In some embodiments, the number of discrete graphene varactors can be from about 1 to about 50.

Each of the discrete graphene varactors suitable for use herein can include at least a portion of one or more electrical circuits. By way of example, in some embodiments, each of the discrete graphene varactors can include one or more passive electrical circuits. In some embodiments, the graphene varactors can be included such that they are integrated directly on an electronic circuit. In some embodiments, the graphene varactors can be included such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a breath sample.

Figure 9:
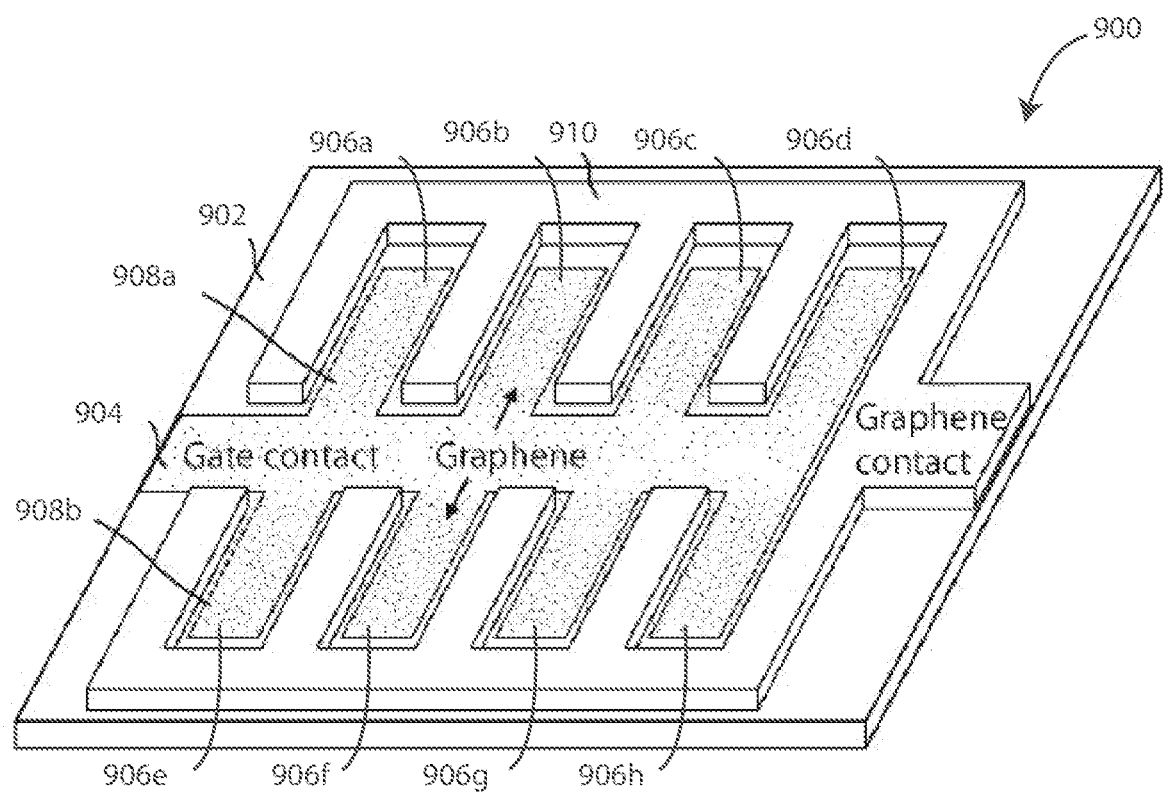
FIG. 9 is a schematic perspective view of a graphene varactor in accordance with various embodiments herein.

In some embodiments, the discrete graphene varactors embodied herein can include graphene-based variable capacitors (or graphene varactors). Referring now to FIG. 9, a schematic view of a graphene varactor 900 is shown in accordance with the embodiments herein. It will be appreciated that graphene varactors can be prepared in various ways with various geometries, and that the graphene varactor shown in FIG. 9 is just one example in accordance with the embodiments herein.

Graphene varactor 900 can include an insulator layer 902, a gate electrode 904 (or "gate contact"), a dielectric layer (not shown in FIG. 9), one or more graphene layers, such as graphene layers 908a and 908b, and a contact electrode 910 (or "graphene contact"). In some embodiments, the graphene layer(s) 908a-b can be contiguous, while in other embodiments the graphene layer(s) 908a-b can be non-contiguous. Gate electrode 904 can be deposited within one or more depressions formed in insulator layer 902. Insulator layer 902 can be formed from an insulative material such as silicon dioxide, formed on a silicon substrate (wafer), and the like. Gate electrode 904 can be formed by an electrically conductive material such as chromium, copper, gold, silver, tungsten, aluminum, titanium, palladium, platinum, iridium, and any combinations or alloys thereof, which can be deposited on top of or embedded within the insulator layer 902. The dielectric layer can be disposed on a surface of the insulator layer 902 and the gate electrode 904. The graphene layer(s) 908a-b can be disposed on the dielectric layer.

Graphene varactor 900 includes eight gate electrode fingers 906a-906h. It will be appreciated that while graphene varactor 900 shows eight gate electrode fingers 906a-906h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Graphene varactor 900 can include one or more contact electrodes 910 disposed on portions of the graphene layers 908a and 908b. Contact electrode 910 can be formed from an electrically conductive material such as chromium, copper, gold, silver, tungsten, aluminum, titanium, palladium, platinum, iridium, and any combinations or alloys thereof. Further aspects of exemplary graphene varactors can be found in U.S. Pat. No. 9,513,244, the content of which is herein incorporated by reference in its entirety.

The capacitance of the graphene varactors can be measured by delivering an excitation current at a particular voltage and/or over a range of voltages. Measuring the capacitance provides data that reflects the binding status of analytes to the graphene varactor(s). Various measurement circuitry can be used to measure the capacitance of the graphene varactor(s).

Figure 10:
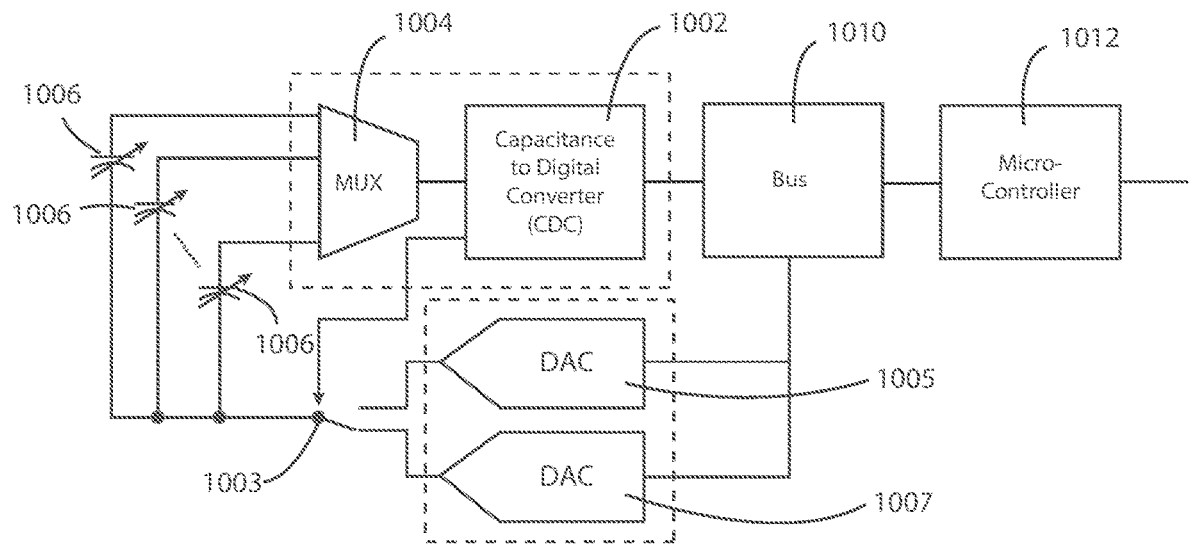
FIG. 10 is a schematic diagram of circuitry to measure the capacitance of a plurality of graphene sensors in accordance with various embodiments herein

Referring now to FIG. 10, a schematic diagram is shown of circuitry to measure the capacitance of a plurality of graphene sensors in accordance with various embodiments herein. The circuitry can include a capacitance to digital converter (CDC) 1002 in electrical communication with a multiplexor 1004. The multiplexor 1004 can provide selective electrical communication with a plurality of graphene varactors 1006. The connection to the other side of the graphene varactors 1006 can be controlled by a switch 1003 (as controlled by the CDC) and can provide selective electrical communication with a first digital to analog converter (DAC) 1005 and a second digital to analog converter (DAC) 1006. The other side of the DACs 1005, 1007 can be connected to a bus device 1010, or in some cases, the CDC 1002. The circuitry can further include a microcontroller 1012, which will be discussed in more detail below.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching. Many different ranges of DC bias voltages can be used. In some embodiments, the range of DC bias voltages can be from −3 V to 3 V, or from −1 V to 1 V, or from −0.5 V to 0.5 V.

Many different aspects can be calculated based on the capacitance data. For example, aspects that can be calculated include maximum slope of capacitance to voltage, change in maximum slope of capacitance to voltage over a baseline value, minimum slope of capacitance to voltage, change in minimum slope of capacitance to voltage over a baseline value, minimum capacitance, change in minimum capacitance over a baseline value, voltage at minimum capacitance (Dirac point), change in voltage at minimum capacitance, maximum capacitance, change in maximum capacitance, ratio of maximum capacitance to minimum capacitance, response time constants, and ratios of any of the foregoing between different graphene sensors and particularly between different graphene sensors having specificity for different analytes.

The above calculated aspects can be used for various diagnostic purposes. In some cases, the above calculated aspects can be indicative of the identity and/or concentrations of specific volatile organic components of a gas sample. As such, each of the calculated values above can serve as a distinct piece of data that forms part of a pattern for a given subject and/or given gas sample. As also described elsewhere herein, the pattern can then be matched against preexisting patterns, or patterns identified in real-time, derived from large stored data sets through techniques such as machine learning or other techniques, wherein such patterns are determined to be characteristic of various conditions or disease states. The above calculated aspects can also be put to other purposes, diagnostic and otherwise.

In some embodiments, calculations such as those described above can be performed by a controller circuit. The controller circuit can be configured to receive an electrical signal reflecting the capacitance of the graphene varactors. In some embodiments, the controller circuit can include a microcontroller to perform these calculations. In some embodiments, the controller circuit can include a microprocessor in electrical communication with the measurement circuit. The microprocessor system can include components such as an address bus, a data bus, a control bus, a clock, a CPU, a processing device, an address decoder, RAM, ROM and the like. In some embodiments, the controller circuit can include a calculation circuit (such as an application specific integrated circuit—ASIC) in electrical communication with the measurement circuit.

In addition, in some embodiments, the system can include a nonvolatile memory where sensitivity calibration information for the particular sensor is stored. By way of example, the sensor could be tested in a production facility, where its sensitivity to various analytes such as VOC's can be determined and then stored on an EPROM or similar component. In addition, or alternatively, sensitivity calibration information can be stored in a central database and referenced with a sensor serial number when subject data is sent to a central location for analysis and diagnosis. These components can be included with any of the pieces of hardware described herein.

In some embodiments herein, components can be configured to communicate over a network, such as the internet or a similar network. In various embodiments, a central storage and data processing facility can be included. In some embodiments, data gathered from sensors in the presence of the subject (local) can be sent to the central processing facility (remote) via the internet or a similar network, and the pattern from the particular subject being evaluated can be compared to those of thousands or millions of other subjects, many of whom have been previously diagnosed with various conditions and wherein such condition data has been stored. Pattern matching algorithms can be used to find other subjects or classes of subjects (for example disease or condition specific classes) to which the current subject's pattern is most similar. Each class of subjects can include a predetermined likelihood of having a given condition or disease state. In this manner, after pattern matching a likelihood of having a given condition or disease state can be provided back across the data network to the facility where the subject is currently located.

In some embodiments, circuitry can include active and passive sensing circuits. Such circuitry can implement wired (direct electrical contact) or wireless sensing techniques.

Figure 11:
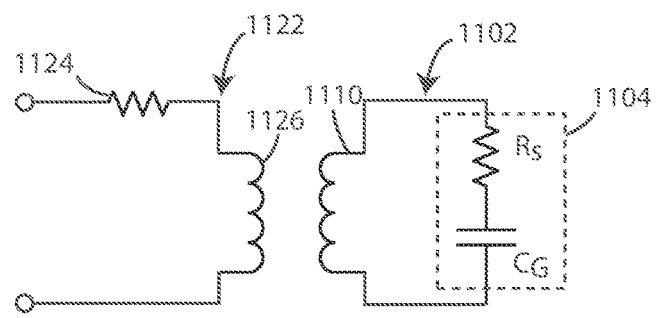
FIG. 11 is a circuit diagram of a passive sensor circuit and a portion of a reading circuit is shown in accordance with various embodiments herein.

The breath sensing systems described herein can include various types of circuitry for generating signals from the discrete graphene varactors. Such circuitry can include active and passive sensing circuits. Such circuitry can implement wired (direct electrical contact) or wireless sensing techniques. Referring now to FIG. 11, a schematic diagram of a passive sensor circuit 1102 and a portion of a reading circuit 1122 is shown in accordance with various aspects herein. In some embodiments, the passive sensor circuit 1102 can include a metal-oxide-graphene varactor 1104 (wherein RS represents the series resistance and CG represents the varactor capacitor) coupled to an inductor 1110. In some embodiments, the reading circuit 1122 can include a reading coil having a resistance 1124 and an inductance 1126. However, it will be appreciated that the circuits shown in FIGS. 10 and 11 are merely exemplary approaches. Many different approaches are contemplated herein. Additional systems and methods for analyte sensing in physiological gas samples are described in co-pending U.S. Pat. No. 10,852,264, which is herein incorporated by reference in its entirety.

Figure 12:
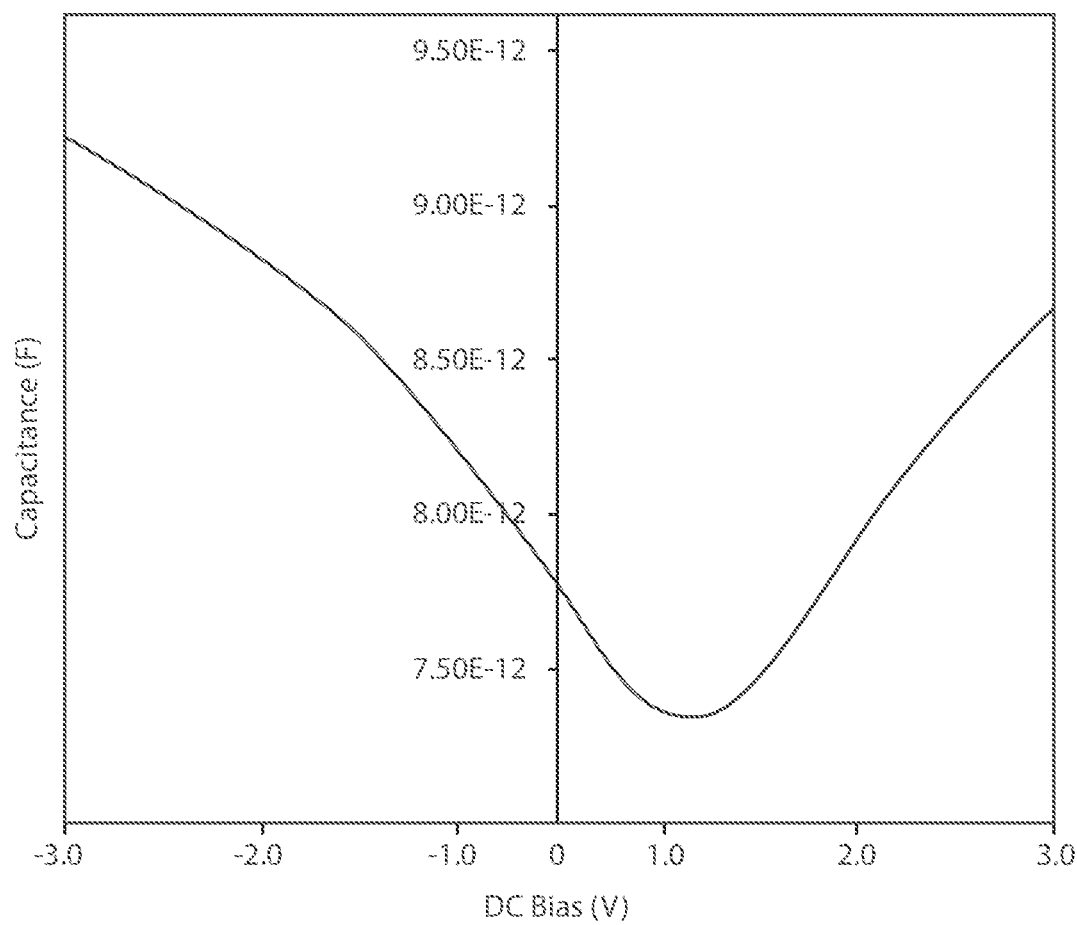
FIG. 12 is a graph showing capacitance versus DC bias voltage for a graphene varactor in accordance with various embodiments herein.

Referring now to FIG. 12 a graph showing capacitance versus DC bias voltage for a graphene varactor is shown in accordance with various embodiments herein. A capacitance to voltage curve like that shown in FIG. 12 can be established by measuring capacitance over a range of bias voltages while exposing the chemical sensor to the exhaled breath of a subject using an LCR meter. In some embodiments, the range of bias voltages can include from −3 V to 3 V. In some embodiments, the range of DC bias voltages can be from −2 V to 2 V, or from −1.5 V to 1.5 V, or from −1 V to 1 V, or from −0.5 V to 0.5 V.

Classification and Pattern Matching

Classifying the sample data set into one or more preestablished brain condition classifications can be performed according to many different machine learning techniques, such as pattern recognition. Classification can include comparing the sample data set against one or more previously determined patterns using a pattern matching or pattern recognition algorithm to determine the pattern that is the best match, wherein the specific previously determined pattern that is the best match indicates the brain condition of the patient.

By way of example, patterns amongst large sets of patient data may be originally identified through machine learning analysis or another similar algorithmic technique. Patterns associated with specific brain condition classifications can be derived from labeled "training" data (supervised learning) or in the absence of labeled data (unsupervised learning).

Algorithms for pattern matching used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Classification algorithms can include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms can include categorical mixture models, deep learning methods, hierarchical clustering, K-means clustering, correlation clustering, and kernel principal component analysis. Ensemble learning algorithms can include boosting, bootstrap aggregating, ensemble averaging, and mixture of experts. General algorithms for predicting arbitrarily-structured sets of labels can include Bayesian networks and Markov random fields. Multilinear subspace learning algorithms can include multilinear principal component analysis (MPCA). Real-valued sequence labeling algorithms can include Kalman filters and particle filters. Regression algorithms can include both supervised (such as Gaussian process regression, linear regression, neural networks and deep learning methods) and unsupervised (such as independent component analysis and principal components analysis) approaches. Sequence labeling algorithms can include both supervised (such as conditional random fields, hidden Markov models, maximum entropy Markov models, and recurrent neural networks) and unsupervised (hidden Markov models and dynamic time warping) approaches.

Many different classifications can be used for the conditions discussed herein. Classifications herein can include, but are not limited to, degrees of a given condition (such as non-existent vs. mild vs. severe). Classifications herein can include, but are not limited to, probabilities that a given condition is present (such as no indication vs. low probability vs high probability).

Methods of Treating

Embodiments herein can specifically include methods of treating a brain condition in a subject. The method can include obtaining an exhaled breath sample from a subject and contacting it with a chemical sensor element, the chemical sensor element comprising a plurality of discrete graphene varactors. The method can further include sensing and storing capacitance of the discrete graphene varactors to obtain a sample data set. The method can further include classifying the sample data set into one or more preestablished brain condition classifications. The method can further include treating the patient based on the brain condition classification. By way of example, one exemplary set of classifications and possible treatments for traumatic brain injury are provided below in Table 1.

TABLE 1

| Traumatic Brain Injury (TBI) Classification | Treatment Examples |
| --- | --- |
| No Indication of TBI | NA |
| Indication of Mild TBI | Cessation of Activity, Follow-Up Monitoring, OTC Pain Relievers |
| Indication of Severe TBI | Drug Therapies Including One or More of Diuretics, Anti-Seizure Drugs, and Coma-Inducing Drugs; Referral for Surgical Therapies Including One or More of Removing Hematomas, Repairing Skull Fracture, Surgery to Stop Bleeding in the Brain, and Opening a Window in the Skull |

By way of example, one exemplary set of classifications and possible treatments for ischemic brain injury are provided below in Table 2.

TABLE 2

| Ischemic Brain Injury Classification | Treatment Examples |
| --- | --- |
| No Indication of Ischemic Brain Injury | NA |
| Low Probability of Ischemic Brain Injury | Cessation of Inducing Activity, Follow-Up Monitoring; Testing for Blood Pressure, Cholesterol, Lipid Levels, Blood Sugar |
| High Probability of Ischemic Brain Injury | Immediate Initiation of/Referral for Surgical and Nonsurgical Therapies; Administration of tissue plasminogen activator |

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A system for detecting, treating, and/or monitoring a brain injury in a subject, comprising:
  a controller circuit; and
  a chemical sensor element, the chemical sensor element comprising a plurality of discrete graphene varactors;
  wherein the system is configured to
  receive a breath sample from the subject and contact the same with the chemical sensor element;
  sense and store capacitance of the discrete graphene varactors across a range of bias voltages to obtain a sample data set;
  classify the sample data set into one or more preestablished brain condition classifications by comparing the sample data set against one or more previously determined patterns using a pattern matching or a pattern recognition algorithm, wherein the one or more previously determined patterns are characteristic of specific brain condition states;
  identify the subject as having a severe traumatic brain injury;
  and initiate a surgical therapy to the subject, wherein the surgical therapy is selected from a group consisting of removing a hematoma, repairing a skull fracture, stopping a brain bleed, and opening a window in a skull of the subject.

2. The system of claim 1, wherein the system is configured to receive a breath sample within 10 minutes following the brain injury.

3. The system of claim 1, wherein the system is configured to receive a breath sample at least two times over a period of 24 hours following an onset of the brain injury.

4. The system of claim 3, wherein the system is configured to analyze the sample data set to determine an improvement or a worsening in the brain injury of the subject over 24 hours.

5. The system of claim 1, wherein the brain injury is at least one of a chronic condition, a subacute condition, and an acute condition.

6. The system of claim 1, wherein the breath sample is received from the subject prior to the subject participating in a sporting event.

7. The system of claim 1, wherein the breath sample is received from the subject prior to the subject participating in a sporting event and is performed at least one additional time after the sporting event begins or is completed.

8. The system of claim 1, wherein the range of bias voltages is from −3 V to 3 V.

9. The system of claim 1, wherein at least 40 discrete capacitance values are stored for each graphene varactor across the range of bias voltages.

10. The system of claim 1, wherein volatile organic compounds (VOCs) from the breath sample interface with the discrete graphene varactors to influence sensed capacitance.

11. The system of claim 1, wherein the plurality of discrete graphene varactors are functionalized with polar compounds having a dipole moment from 1.5 D to 5 D.

12. The system of claim 1, wherein the system is further configured to store additional data regarding the subject beyond sensed capacitance as part of the sample data set that is classified.

13. The system of claim 12, the additional data comprising at least one of:
  prior traumatic brain injuries of the subject;
  an amount of elapsed time since an event has occurred which resulted in an injury to the subject;
  age of the subject;
  results of a neurological examination;
  symptoms experienced by the subject; and
  data regarding specific biomarkers of a brain condition.

14. The system of claim 1, wherein the system is configured to further analyze the sample data set to identify if the subject is a candidate for drug therapy for the brain injury.

15. The system of claim 1, wherein, after the system has initiated a surgical therapy to the subject, the system is configured to monitor progress in response to the surgical therapy by receiving a breath sample from the subject and contacting the same with the chemical sensor element; sensing and storing capacitance of the discrete graphene varactors across a range of bias voltages to obtain a sample data set; and classifying the sample data set into one or more preestablished brain condition classifications.

16. A system for detecting, treating, and/or monitoring a brain injury in a subject, comprising:
  a controller circuit; and
  a chemical sensor element, the chemical sensor element comprising a plurality of discrete graphene varactors;
  wherein the system is configured to
  receive a breath sample from the subject and contact the same with the chemical sensor element;
  sense and store capacitance of the discrete graphene varactors across a range of bias voltages to obtain a sample data set;
  classify the sample data set into one or more preestablished brain condition classifications by comparing the sample data set against one or more previously determined patterns using a pattern matching or a pattern recognition algorithm, wherein the one or more previously determined patterns are characteristic of specific brain condition states;
  identify the subject as having a mild traumatic brain injury; and
  initiate a treatment to the subject, wherein the treatment comprises the administration of over-the-counter (OTC) pain relieving drugs capable of treating the mild traumatic brain injury to the subject.

* * * * *